United States Patent [19]
Chatterjee et al.

[11] Patent Number: 5,932,440
[45] Date of Patent: Aug. 3, 1999

[54] MAMMALIAN RIBONUCLEASE INHIBITORS AND USE THEREOF

[75] Inventors: Deb K. Chatterjee, N. Potomac; Harini Shandilya, New Market, both of Md.

[73] Assignee: Life Technologies, Inc., Rockville, Md.

[21] Appl. No.: 08/910,731

[22] Filed: Aug. 13, 1997

Related U.S. Application Data

[63] Continuation-in-part of application No. 08/795,395, Feb. 4, 1997, which is a continuation-in-part of application No. 08/794,546, Feb. 3, 1997, abandoned

[60] Provisional application No. 60/024,057, Aug. 16, 1996.

[51] Int. Cl.$^6$ .............................. C12P 21/06; C07H 1/20; C12N 5/00; C12N 5/10
[52] U.S. Cl. .................... 435/69.1; 536/23.5; 435/320.1; 435/325; 435/252.3; 435/252.33; 435/419
[58] Field of Search .................................. 536/23.5, 23.4; 435/194, 320.1, 325, 419, 252.3, 252.33, 69.1; 530/350

[56] References Cited

U.S. PATENT DOCUMENTS

| | | | |
|---|---|---|---|
| 4,966,964 | 10/1990 | Shapiro et al. | 536/27 |
| 5,019,556 | 5/1991 | Shapiro et al. | 514/2 |
| 5,266,687 | 11/1993 | Shapiro et al. | 536/23.1 |
| 5,552,302 | 9/1996 | Lewis et al. | 435/692 |

OTHER PUBLICATIONS

Blackburn, P., et al., "Ribonuclease Inhibitor from Human Placenta," *J. Biol. Chem.* 252(16):5904–5910 (1977).
Blackburn, P., "Ribonuclease Inhibitor from Human Placenta: Rapid Purification and Assay," *J. Biol. Chem.* 254(24):12484–12487 (1979).
Burton, L.E., et al., "Ribonuclease Inhibitor from Bovine Brain," *Int. J. Peptide Protein Res.* 16:359–364 (1980).
Hofsteenge, J., et al., "Amino Acid Sequence of the Ribonuclease Inhibitor from Porcine Liver Reveals the Presence of Leucine–Rich Repeats," *Biochemistry* 27:8537–8544 (1988).
Humphreys, D.P., et al., "Human Protein Disulfide Isomerase Fuctionally Complements a dsbA Mutation and Enhances the Yield of Pectate Lyase C in *Escherichia coli*," *J. Biol. Chem.* 270(47):28210–28215 (1995).

Kawanomoto, M., et al., "cDNA cloning and sequence of rat ribonuclease inhibitor, and tissue distribution of the mRNA," *Biochim. Biophys. Acta* 1129:335–338 (1992).
Burton, L.E., and Fucci, N.P., "Ribonuclease inhibitors from the livers of five mammalian species," *Int. J. Peptide Protein Res.* 19:372–379 (1982).
Chopra, A.K., et al., "Improved synthesis of *Salmonella typhimurium* enterotixin using gene fusion expression systems," *Gene* 144:81–85 (1994).
Gentz, R., et al., "Bioassay for trans–activation using purified human immunodeficiency virus tat–encoded protein: Trans–activation requires mRNA synthesis," *Proc. Natl. Acad. Sci. USA* 86:821–824 (1989).
Kobe, B., and Diesenhofer, J., "Crystal structure of porcine ribonuclease inhibitor, a protein with leucine–rich repeats," *Nature* 336:751–756 (1993).
Lee, F.S., et al., "Primary Structure of Human Placental Ribonuclease Inhibitor," *Biochemistry* 27:8545–8553 (1988).
Neumann, U., et al., "Crystallization of Porcine Liver Ribonuclease Inhibitor a Member of the Family of Proteins Containing Leucine–rich Repeats," *J. Mol. Biol.* 231:505–508 (1993).
Vicentini, A.M., et al., "Protein Chemical and Kinetic Characterization of Recombinant Porcine Ribonuclease Inhibitor Expressed in *Saccharomyces cerevisiae*," *Biochemistry* 29:8827–8834 (1990).
Wilson, I.A., et al., "The Structure of an Antigenic Determinant in a Protein," *Cell* 37:767–778 (1984).

*Primary Examiner*—Robert A. Wax
*Assistant Examiner*—Maryam Monshipouri
*Attorney, Agent, or Firm*—Sterne, Kessler Goldstein & Fox P.L.L.C.

[57] ABSTRACT

The invention relates to the cloning of a gene encoding rat liver RI, and its expression in a cellular host. In addition, the invention relates to the successful cloning of a gene encoding porcine liver RI, and its expression in a cellular host. The invention also relates to the cloning and expression of human liver RI, and the cloning and expression of chimeric mammalian RIs, particularly chimeric porcine/human liver RIs, which may be thermostable. The invention also relates to methods and kits for use in producing nucleic acid molecules and polypeptides using the RIs of the invention, and to nucleic acid molecules and polypeptides produced using these methods and kits.

44 Claims, 5 Drawing Sheets ic Acta. 1129: 335–338 (1992)) is known.

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
        (A) LENGTH: 1371 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..1368

(xi) SEQUENCE DESCRIPTION: SEQ ID NO:1:

```
ATG AAC CTC GAT ATT CAT TGC GAG CAG CTG AGC GAC GCC CGG TGG ACA        48
Met Asn Leu Asp Ile His Cys Glu Gln Leu Ser Asp Ala Arg Trp Thr
 1               5                  10                  15

GAG CTC CTG CCG CTG CTC CAG CAG TAT GAG GTG GTC AGG CTC GAC GAC        96
Glu Leu Leu Pro Leu Leu Gln Gln Tyr Glu Val Val Arg Leu Asp Asp
            20                  25                  30

TGC GGC CTC ACG GAG GAG CAC TGC AAG GAC ATC GGT TCT GCC CTC CGG       144
Cys Gly Leu Thr Glu Glu His Cys Lys Asp Ile Gly Ser Ala Leu Arg
        35                  40                  45
```

| | | |
|---|---|---|
| GCC AAC CCC TCC CTG ACC GAG CTC TGC CTC CGC ACC AAC GAG CTG GGC<br>Ala Asn Pro Ser Leu Thr Glu Leu Cys Leu Arg Thr Asn Glu Leu Gly<br>50                        55                    60 | | 192 |
| GAT GCC GGC GTG CAC CTG GTG CTG CAG GGC CTG CAG AGC CCC ACC TGC<br>Asp Ala Gly Val His Leu Val Leu Gln Gly Leu Gln Ser Pro Thr Cys<br>65                       70                   75                  80 | | 240 |
| AAG ATC CAG AAG CTC AGC CTG CAG AAC TGC TCC CTG ACC GAG GCG GGC<br>Lys Ile Gln Lys Leu Ser Leu Gln Asn Cys Ser Leu Thr Glu Ala Gly<br>                 85                   90                   95 | | 288 |
| TGC GGG GTC CTG CCC AGC ACG CTG CGC TCC CTG CCC ACG CTG CGG GAG<br>Cys Gly Val Leu Pro Ser Thr Leu Arg Ser Leu Pro Thr Leu Arg Glu<br>             100                   105                110 | | 336 |
| CTG CAT CTC AGC GAC AAC CCA CTG GGG GAC GCC GGC CTG CGG CTG CTC<br>Leu His Leu Ser Asp Asn Pro Leu Gly Asp Ala Gly Leu Arg Leu Leu<br>             115                   120                125 | | 384 |
| TGT GAG GGG CTC CTG GAC CCC CAG TGC CAC CTG GAG AAG CTG CAG TTG<br>Cys Glu Gly Leu Leu Asp Pro Gln Cys His Leu Glu Lys Leu Gln Leu<br>130                        135                  140 | | 432 |
| GAG TAC TGC CGC CTG ACG GCC GCC AGC TGC GAG CCC CTG GCC TCG GTG<br>Glu Tyr Cys Arg Leu Thr Ala Ala Ser Cys Glu Pro Leu Ala Ser Val<br>145                        150                  155                160 | | 480 |
| CTC AGG GCC ACG CGG GCC TTG AAG GAG CTC ACG GTG AGC AAC AAC GAC<br>Leu Arg Ala Thr Arg Ala Leu Lys Glu Leu Thr Val Ser Asn Asn Asp<br>             165                   170                175 | | 528 |
| ATC GGC GAG GCC GGC GCC CGG GTG CTG GGC CAG GGT CTG GCA GAC TCT<br>Ile Gly Glu Ala Gly Ala Arg Val Leu Gly Gln Gly Leu Ala Asp Ser<br>                 180                   185                190 | | 576 |
| GCC TGC CAG CTG GAG ACG CTC AGG CTG GAG AAC TGC GGT CTC ACG CCA<br>Ala Cys Gln Leu Glu Thr Leu Arg Leu Glu Asn Cys Gly Leu Thr Pro<br>             195                   200                205 | | 624 |
| GCC AAC TGC AAA GAC CTG TGC GGA ATT GTG GCC TCC CAG GCC TCG CTG<br>Ala Asn Cys Lys Asp Leu Cys Gly Ile Val Ala Ser Gln Ala Ser Leu<br>210                        215                  220 | | 672 |
| AGG GAG CTT GAC CTG GGC AGC AAC GGG CTG GGC GAC GCG GGC ATA GCC<br>Arg Glu Leu Asp Leu Gly Ser Asn Gly Leu Gly Asp Ala Gly Ile Ala<br>225                        230                  235                240 | | 720 |
| GAG CTG TGC CCC GGG CTC TTG AGC CCC GCC TCC CGC CTC AAG ACC CTG<br>Glu Leu Cys Pro Gly Leu Leu Ser Pro Ala Ser Arg Leu Lys Thr Leu<br>                 245                   250                255 | | 768 |
| TGG CTC TGG GAG TGT GAC ATC ACC GCC AGT GGC TGC AGA GAC CTC TGC<br>Trp Leu Trp Glu Cys Asp Ile Thr Ala Ser Gly Cys Arg Asp Leu Cys<br>                 260                   265                270 | | 816 |
| CGT GTC CTC CAG GCC AAG GAG ACC CTG AAG GAG CTC AGT CTG GCG GGC<br>Arg Val Leu Gln Ala Lys Glu Thr Leu Lys Glu Leu Ser Leu Ala Gly<br>             275                   280                285 | | 864 |
| AAC AAG CTG GGC GAC GAG GGC GCC CGG CTG CTG TGC GAG AGC CTG CTG<br>Asn Lys Leu Gly Asp Glu Gly Ala Arg Leu Leu Cys Glu Ser Leu Leu<br>290                        295                  300 | | 912 |
| CAG CCC GGC TGC CAG CTG GAG TCC CTG TGG GTG AAG TCC TGC AGC CTC<br>Gln Pro Gly Cys Gln Leu Glu Ser Leu Trp Val Lys Ser Cys Ser Leu<br>305                        310                  315                320 | | 960 |
| ACG GCG GCC TGC TGC CAG CAC GTC AGC TTG ATG CTG ACC CAG AAC AAG<br>Thr Ala Ala Cys Cys Gln His Val Ser Leu Met Leu Thr Gln Asn Lys<br>                 325                   330                335 | | 1008 |
| CAT CTC CTG GAA CTT CAG TTG AGC AGC AAC AAG CTG GGT GAC TCT GGC<br>His Leu Leu Glu Leu Gln Leu Ser Ser Asn Lys Leu Gly Asp Ser Gly<br>             340                   345                350 | | 1056 |
| ATC CAG GAG CTG TGC CAG GCC CTG AGC CAG CCG GGC ACC ACA CTG CGG<br>Ile Gln Glu Leu Cys Gln Ala Leu Ser Gln Pro Gly Thr Thr Leu Arg<br>             355                   360                365 | | 1104 |

```
GTG CTC TGT CTT GGG GAC TGT GAG GTG ACC AAC AGC GGC TGC AGC AGC      1152
Val Leu Cys Leu Gly Asp Cys Glu Val Thr Asn Ser Gly Cys Ser Ser
    370                     375                 380

CTC GCC TCG CTC CTG CTG GCC AAC CGC AGC CTG CGA GAG CTG GAC CTG      1200
Leu Ala Ser Leu Leu Leu Ala Asn Arg Ser Leu Arg Glu Leu Asp Leu
385                 390                 395                 400

AGC AAC AAC TGT GTG GGC GAC CCG GGC GTC CTG CAG CTG CTG GGG AGC      1248
Ser Asn Asn Cys Val Gly Asp Pro Gly Val Leu Gln Leu Leu Gly Ser
                405                 410                 415

CTG GAG CAG CCG GGC TGC GCC CTG GAG CAG CTG GTC CTG TAC GAC ACC      1296
Leu Glu Gln Pro Gly Cys Ala Leu Glu Gln Leu Val Leu Tyr Asp Thr
            420                 425                 430

TAC TGG ACG GAG GAG GTG GAG GAC CGC CTG CAG GCC CTG GAG GGG AGC      1344
Tyr Trp Thr Glu Glu Val Glu Asp Arg Leu Gln Ala Leu Glu Gly Ser
        435                 440                 445

AAG CCC GGC CTG AGG GTC ATC TCC TGA                                  1371
Lys Pro Gly Leu Arg Val Ile Ser
    450                 455
```

(2) INFORMATION FOR SEQ ID NO:2:

(i) SEQUENCE CHARACTERISTICS:
        (A) LENGTH: 456 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Leu Asp Ile His Cys Glu Gln Leu Ser Asp Ala Arg Trp Thr
1               5                   10                  15

Glu Leu Leu Pro Leu Leu Gln Gln Tyr Glu Val Val Arg Leu Asp Asp
                20                  25                  30

Cys Gly Leu Thr Glu Glu His Cys Lys Asp Ile Gly Ser Ala Leu Arg
            35                  40                  45

Ala Asn Pro Ser Leu Thr Glu Leu Cys Leu Arg Thr Asn Glu Leu Gly
        50                  55                  60

Asp Ala Gly Val His Leu Val Leu Gln Gly Leu Gln Ser Pro Thr Cys
65                  70                  75                  80

Lys Ile Gln Lys Leu Ser Leu Gln Asn Cys Ser Leu Thr Glu Ala Gly
                85                  90                  95

Cys Gly Val Leu Pro Ser Thr Leu Arg Ser Leu Pro Thr Leu Arg Glu
            100                 105                 110

Leu His Leu Ser Asp Asn Pro Leu Gly Asp Ala Gly Leu Arg Leu Leu
        115                 120                 125

Cys Glu Gly Leu Leu Asp Pro Gln Cys His Leu Glu Lys Leu Gln Leu
130                 135                 140

Glu Tyr Cys Arg Leu Thr Ala Ala Ser Cys Glu Pro Leu Ala Ser Val
145                 150                 155                 160

Leu Arg Ala Thr Arg Ala Leu Lys Glu Leu Thr Val Ser Asn Asn Asp
                165                 170                 175

Ile Gly Glu Ala Gly Ala Arg Val Leu Gly Gln Gly Leu Ala Asp Ser
            180                 185                 190

Ala Cys Gln Leu Glu Thr Leu Arg Leu Glu Asn Cys Gly Leu Thr Pro
        195                 200                 205

Ala Asn Cys Lys Asp Leu Cys Gly Ile Val Ala Ser Gln Ala Ser Leu
210                 215                 220

Arg Glu Leu Asp Leu Gly Ser Asn Gly Leu Gly Asp Ala Gly Ile Ala
225                 230                 235                 240
```

```
Glu Leu Cys Pro Gly Leu Leu Ser Pro Ala Ser Arg Leu Lys Thr Leu
                245                 250                 255

Trp Leu Trp Glu Cys Asp Ile Thr Ala Ser Gly Cys Arg Asp Leu Cys
            260                 265                 270

Arg Val Leu Gln Ala Lys Glu Thr Leu Lys Glu Leu Ser Leu Ala Gly
        275                 280                 285

Asn Lys Leu Gly Asp Glu Gly Ala Arg Leu Leu Cys Glu Ser Leu Leu
    290                 295                 300

Gln Pro Gly Cys Gln Leu Glu Ser Leu Trp Val Lys Ser Cys Ser Leu
305                 310                 315                 320

Thr Ala Ala Cys Cys Gln His Val Ser Leu Met Leu Thr Gln Asn Lys
                325                 330                 335

His Leu Leu Glu Leu Gln Leu Ser Ser Asn Lys Leu Gly Asp Ser Gly
            340                 345                 350

Ile Gln Glu Leu Cys Gln Ala Leu Ser Gln Pro Gly Thr Thr Leu Arg
        355                 360                 365

Val Leu Cys Leu Gly Asp Cys Glu Val Thr Asn Ser Gly Cys Ser Ser
    370                 375                 380

Leu Ala Ser Leu Leu Leu Ala Asn Arg Ser Leu Arg Glu Leu Asp Leu
385                 390                 395                 400

Ser Asn Asn Cys Val Gly Asp Pro Gly Val Leu Gln Leu Leu Gly Ser
                405                 410                 415

Leu Glu Gln Pro Gly Cys Ala Leu Glu Gln Leu Val Leu Tyr Asp Thr
            420                 425                 430

Tyr Trp Thr Glu Glu Val Glu Asp Arg Leu Gln Ala Leu Glu Gly Ser
        435                 440                 445

Lys Pro Gly Leu Arg Val Ile Ser
    450                 455

(2) INFORMATION FOR SEQ ID NO:3:

(i) SEQUENCE CHARACTERISTICS:
        (A) LENGTH: 1374 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..1368

(xi) SEQUENCE DESCRIPTION: SEQ ID NO:3:

ATG AGT CTT GAC ATC CAG TGT GAG CAG CTG AGT GAT GCC CGG TGG ACA        48
Met Ser Leu Asp Ile Gln Cys Glu Gln Leu Ser Asp Ala Arg Trp Thr
1               5                   10                  15

GAG CTC CTT CCC CTG ATC CAA CAA TAC CAA GTG GTC AGG CTG GAT GAC        96
Glu Leu Leu Pro Leu Ile Gln Gln Tyr Gln Val Val Arg Leu Asp Asp
            20                  25                  30

TGT GGC CTC ACT GAA GTG CGG TGC AAA GAC ATC AGG TCA GCG ATC CAG       144
Cys Gly Leu Thr Glu Val Arg Cys Lys Asp Ile Arg Ser Ala Ile Gln
        35                  40                  45

GCC AAC CCT GCC CTG ACA GAG CTC AGC CTA CGC ACC AAT GAA CTG GGT       192
Ala Asn Pro Ala Leu Thr Glu Leu Ser Leu Arg Thr Asn Glu Leu Gly
    50                  55                  60

GAT GCT GGT GTG GGT CTG GTG CTC CAG GGC CTG CAG AAT CCC ACT TGT       240
Asp Ala Gly Val Gly Leu Val Leu Gln Gly Leu Gln Asn Pro Thr Cys
65                  70                  75                  80
```

-continued

| | |
|---|---|
| AAG ATC CAG AAG CTG AGC CTT CAG AAC TGC AGC TTG ACG GAA GCT GGC<br>Lys Ile Gln Lys Leu Ser Leu Gln Asn Cys Ser Leu Thr Glu Ala Gly<br>      85          90         95 | 288 |
| TGT GGG GTC CTG CCT GAT GTG CTG CGC TCT TTG TCT ACC CTG CGT GAA<br>Cys Gly Val Leu Pro Asp Val Leu Arg Ser Leu Ser Thr Leu Arg Glu<br>    100          105         110 | 336 |
| CTA CAT CTC AAT GAC AAC CCT CTG GGG GAT GAA GGC CTG AAG CTG CTC<br>Leu His Leu Asn Asp Asn Pro Leu Gly Asp Glu Gly Leu Lys Leu Leu<br> 115         120         125 | 384 |
| TGT GAA GGA CTC CGG GAC CCC CAG TGC CGT CTT GAG AAG CTT CAG TTG<br>Cys Glu Gly Leu Arg Asp Pro Gln Cys Arg Leu Glu Lys Leu Gln Leu<br>130         135         140 | 432 |
| GAA TAC TGT AAC CTC ACA GCT ACC AGC TGC GAG CCC CTG GCC TCA GTG<br>Glu Tyr Cys Asn Leu Thr Ala Thr Ser Cys Glu Pro Leu Ala Ser Val<br>145         150         155         160 | 480 |
| CTC AGG GTG AAA CCT GAC TTT AAA GAG CTA GTA TTG AGC AAC AAT GAC<br>Leu Arg Val Lys Pro Asp Phe Lys Glu Leu Val Leu Ser Asn Asn Asp<br>         165         170         175 | 528 |
| TTC CAT GAG GCT GGT ATC CAC ACT CTG TGC CAG GGC CTG AAG GAT TCT<br>Phe His Glu Ala Gly Ile His Thr Leu Cys Gln Gly Leu Lys Asp Ser<br>         180         185         190 | 576 |
| GCC TGT CAA CTG GAG TCA CTC AAA CTG GAG AAC TGT GGT ATC ACA TCA<br>Ala Cys Gln Leu Glu Ser Leu Lys Leu Glu Asn Cys Gly Ile Thr Ser<br>         195         200         205 | 624 |
| GCC AAC TGC AAG GAT CTG TGT GAT GTT GTG GCC TCC AAA GCC TCA CTG<br>Ala Asn Cys Lys Asp Leu Cys Asp Val Val Ala Ser Lys Ala Ser Leu<br>210         215         220 | 672 |
| CAA GAA CTG GAC TTG GGC AGC AAC AAG CTG GGC AAC ACA GGC ATT GCA<br>Gln Glu Leu Asp Leu Gly Ser Asn Lys Leu Gly Asn Thr Gly Ile Ala<br>225         230         235         240 | 720 |
| GCA CTG TGC TCA GGA CTG CTG CTT CCC AGC TGC AGG CTG AGG ACT CTG<br>Ala Leu Cys Ser Gly Leu Leu Leu Pro Ser Cys Arg Leu Arg Thr Leu<br>         245         250         255 | 768 |
| TGG CTC TGG GAC TGT GAT GTC ACT GCA GAA GGC TGC AAG GAC CTG TGC<br>Trp Leu Trp Asp Cys Asp Val Thr Ala Glu Gly Cys Lys Asp Leu Cys<br>         260         265         270 | 816 |
| CGT GTC CTC AGA GCC AAG CAG AGC CTG AAG GAA CTC AGC CTA GCT GGC<br>Arg Val Leu Arg Ala Lys Gln Ser Leu Lys Glu Leu Ser Leu Ala Gly<br>         275         280         285 | 864 |
| AAT GAG CTG AAG GAT GAG GGT GCC CAA CTG CTG TGT GAG AGC CTG TTA<br>Asn Glu Leu Lys Asp Glu Gly Ala Gln Leu Leu Cys Glu Ser Leu Leu<br>290         295         300 | 912 |
| GAG CCT GGC TGT CAG CTG GAG TCA CTG TGG GTA AAG ACC TGT AGC CTC<br>Glu Pro Gly Cys Gln Leu Glu Ser Leu Trp Val Lys Thr Cys Ser Leu<br>305         310         315         320 | 960 |
| ACA GCT GCC TCT TGT CCC CAC TTC TGC TCG GTG TTG ACC AAA AAC AGT<br>Thr Ala Ala Ser Cys Pro His Phe Cys Ser Val Leu Thr Lys Asn Ser<br>         325         330         335 | 1008 |
| TCT CTG TTT GAG TTG CAA ATG AGC AGC AAC CCG CTG GGA GAC TCG GGA<br>Ser Leu Phe Glu Leu Gln Met Ser Ser Asn Pro Leu Gly Asp Ser Gly<br>         340         345         350 | 1056 |
| GTC GTG GAG CTT TGC AAG GCC CTG GGC TAT CCG GAC ACA GTG CTG CGT<br>Val Val Glu Leu Cys Lys Ala Leu Gly Tyr Pro Asp Thr Val Leu Arg<br>         355         360         365 | 1104 |
| GTG CTT TGG CTG GGA GAC TGT GAT GTG ACA GAC AGT GGC TGC AGC AGC<br>Val Leu Trp Leu Gly Asp Cys Asp Val Thr Asp Ser Gly Cys Ser Ser<br>    370          375         380 | 1152 |
| CTT GCC ACT GTC CTG CTG GCC AAC CGC AGC TTG AGG GAA CTG GAC CTC<br>Leu Ala Thr Val Leu Leu Ala Asn Arg Ser Leu Arg Glu Leu Asp Leu<br>385         390         395         400 | 1200 |

```
AGT AAC AAC TGC ATG GGG GAC AAC GGT GTC CTA CAA CTG CTG GAG AGC              1248
Ser Asn Asn Cys Met Gly Asp Asn Gly Val Leu Gln Leu Leu Glu Ser
            405                 410                 415

CTC AAA CAG CCC AGC TGC ATC CTT CAG CAG CTT GTC CTG TAT GAC ATT              1296
Leu Lys Gln Pro Ser Cys Ile Leu Gln Gln Leu Val Leu Tyr Asp Ile
            420                 425                 430

TAC TGG ACG GAT GAG GTG GAA GAC CAG CTT CGG GCC CTG GAG GAG GAA              1344
Tyr Trp Thr Asp Glu Val Glu Asp Gln Leu Arg Ala Leu Glu Glu Glu
            435                 440                 445

AGG CCA TCC CTG AGG ATC ATT TCC TGATAA                                       1374
Arg Pro Ser Leu Arg Ile Ile Ser
            450                 455

(2) INFORMATION FOR SEQ ID NO:4:

(i) SEQUENCE CHARACTERISTICS:
        (A) LENGTH: 456 amino acids
        (B) TYPE: amino acid
        (D) TOPOLOGY: linear (ii) MOLECULE TYPE: protein (xi) SEQUENCE DESCRIPTION: SEQ ID NO:4:

Met Ser Leu Asp Ile Gln Cys Glu Gln Leu Ser Asp Ala Arg Trp Thr
  1               5                  10                  15

Glu Leu Leu Pro Leu Ile Gln Gln Tyr Gln Val Val Arg Leu Asp Asp
                 20                  25                  30

Cys Gly Leu Thr Glu Val Arg Cys Lys Asp Ile Arg Ser Ala Ile Gln
             35                  40                  45

Ala Asn Pro Ala Leu Thr Glu Leu Ser Leu Arg Thr Asn Glu Leu Gly
         50                  55                  60

Asp Ala Gly Val Gly Leu Val Leu Gln Gly Leu Gln Asn Pro Thr Cys
 65                  70                  75                  80

Lys Ile Gln Lys Leu Ser Leu Gln Asn Cys Ser Leu Thr Glu Ala Gly
                 85                  90                  95

Cys Gly Val Leu Pro Asp Val Leu Arg Ser Leu Ser Thr Leu Arg Glu
            100                 105                 110

Leu His Leu Asn Asp Asn Pro Leu Gly Asp Glu Gly Leu Lys Leu Leu
        115                 120                 125

Cys Glu Gly Leu Arg Asp Pro Gln Cys Arg Leu Glu Lys Leu Gln Leu
130                 135                 140

Glu Tyr Cys Asn Leu Thr Ala Thr Ser Cys Glu Pro Leu Ala Ser Val
145                 150                 155                 160

Leu Arg Val Lys Pro Asp Phe Lys Glu Leu Val Leu Ser Asn Asn Asp
                165                 170                 175

Phe His Glu Ala Gly Ile His Thr Leu Cys Gln Gly Leu Lys Asp Ser
            180                 185                 190

Ala Cys Gln Leu Glu Ser Leu Lys Leu Glu Asn Cys Gly Ile Thr Ser
        195                 200                 205

Ala Asn Cys Lys Asp Leu Cys Asp Val Val Ala Ser Lys Ala Ser Leu
210                 215                 220

Gln Glu Leu Asp Leu Gly Ser Asn Lys Leu Gly Asn Thr Gly Ile Ala
225                 230                 235                 240

Ala Leu Cys Ser Gly Leu Leu Leu Pro Ser Cys Arg Leu Arg Thr Leu
                245                 250                 255

Trp Leu Trp Asp Cys Asp Val Thr Ala Glu Gly Cys Lys Asp Leu Cys
            260                 265                 270
```

```
Arg Val Leu Arg Ala Lys Gln Ser Leu Lys Glu Leu Ser Leu Ala Gly
        275                 280                 285

Asn Glu Leu Lys Asp Glu Gly Ala Gln Leu Leu Cys Glu Ser Leu Leu
    290                 295                 300

Glu Pro Gly Cys Gln Leu Glu Ser Leu Trp Val Lys Thr Cys Ser Leu
305                 310                 315                 320

Thr Ala Ala Ser Cys Pro His Phe Cys Ser Val Leu Thr Lys Asn Ser
                325                 330                 335

Ser Leu Phe Glu Leu Gln Met Ser Ser Asn Pro Leu Gly Asp Ser Gly
            340                 345                 350

Val Val Glu Leu Cys Lys Ala Leu Gly Tyr Pro Asp Thr Val Leu Arg
        355                 360                 365

Val Leu Trp Leu Gly Asp Cys Asp Val Thr Asp Ser Gly Cys Ser Ser
370                 375                 380

Leu Ala Thr Val Leu Leu Ala Asn Arg Ser Leu Arg Glu Leu Asp Leu
385                 390                 395                 400

Ser Asn Asn Cys Met Gly Asp Asn Gly Val Leu Gln Leu Leu Glu Ser
                405                 410                 415

Leu Lys Gln Pro Ser Cys Ile Leu Gln Leu Val Leu Tyr Asp Ile
            420                 425                 430

Tyr Trp Thr Asp Glu Val Glu Asp Gln Leu Arg Ala Leu Glu Glu Glu
        435                 440                 445

Arg Pro Ser Leu Arg Ile Ile Ser
    450                 455

(2) INFORMATION FOR SEQ ID NO:5:

(i) SEQUENCE CHARACTERISTICS:
        (A) LENGTH: 1386 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:5:

ATGAGCCTGG ACATCCAGAG CCTGGACATC CAGTGTGAGG AGCTGAGCGA CGCTAGATGG      60

GCCGAGCTCC TCCCTCTGCT CCAGCAGTGC CAAGTGGTCA GGCTGGACGA CTGTGGCCTC     120

ACGGAAGCAC GGTGCAAGGA CATCAGCTCT GCACTTCGAG TCAACCCTGC ACTGGCAGAG     180

CTCAACCTGC GCAGCAACGA GCTGGGCGAT GTCGGCGTGC ATTGCGTGCT CCAGGGCCTG     240

CAGACCCCCT CCTGCAAGAT CCAGAAGCTG AGCCTCCAGA ACTGCTGCCT GACGGGGGCC     300

GGCTGCGGGG TCCTGTCCAG CACACTACGC ACCCTGCCCA CCCTGCAGGA GCTGCACCTC     360

AGCGACAACC TCTTGGGGGA TGCGGGCCTG CAGCTGCTCT GCGAAGGACT CCTGGACCCC     420

CAGTGCCGCC TGGAAAAGCT GCAGCTGGAG TATTGCAGCC TCTCGGCTGC CAGCTGCGAG     480

CCCCTGGCCT CCGTGCTCAG GGCCAAGCCG GACTTCAAGG AGCTCACGGT TAGCAACAAC     540

GACATCAATG AGGCTGGCGT CCGTGTGCTG TGCCAGGGCC TGAAGGACTC CCCCTGCCAG     600

CTGGAGGCGC TCAAGCTGGA GAGCTGCGGT GTGACATCAG ACAACTGCCG GGACCTGTGC     660

GGCATTGTGG CCTCCAAGGC CTCGCTGCGG GAGCTGGCCC TGGGCAGCAA CAAGCTGGGT     720

GATGTGGGCA TGGCGGAGCT GTGCCCAGGG CTGCTCCACC CCAGCTCCAG GCTCAGGACC     780

CTGTGGATCT GGGAGTGTGG CATCACTGCC AAGGGCTGCG GGATCTGTG CCGTGTCCTC      840

AGGGCCAAGG AGAGCCTGAA GGAGCTCAGC CTGGCCGGCA ACGAGCTGGG GGATGAGGGT     900

GCCCGACTGC TGTGTGAGAC CCTGCTGGAA CCTGGCTGCC AGCTGGAGTC GCTGTGGGTG     960
```

-continued

```
AAGTCCTGCA GCTTCACAGC CGCCTGCTGC CCCCACTTCA GCTCAGTGCT GGCCCAGAAC      1020

AGGTTTCTCC TGGAGCTACA GATAAGCAAC AACAGGCTGG AGGATGCGGG CGTGCGGGAG      1080

CTGTGCCAGG GCCTGGGCCA GCCTGGCTCT GTGCTGCGGG TGCTCTGGTT GGCCGACTGC      1140

GATGTGAGTG ACAGCAGCTG CAGCAGCCTC GCCGCAACCC TGTTGGCCAA CCACAGCCTG      1200

CGTGAGCTGG ACCTCAGCAA CAACTGCCTG GGGGACGCCG GCATCCTGCA GCTGGTGGAG      1260

AGCGTCCGGC AGCCGGGCTG CCTCCTGGAG CAGCTGGTCC TGTACGACAT TTACTGGTCT      1320

GAGGAGATGG AGGACCGGCT GCAGGCCCTG GAGAAGGACA AGCCATCCCT GAGGGTCATC      1380

TCCTGA                                                                 1386
```

(2) INFORMATION FOR SEQ ID NO:6:

(i) SEQUENCE CHARACTERISTICS:
        (A) LENGTH: 461 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:6:

```
Met Ser Leu Asp Ile Gln Ser Leu Asp Ile Gln Cys Glu Glu Leu Ser
  1               5                  10                  15

Asp Ala Arg Trp Ala Glu Leu Leu Pro Leu Gln Gln Cys Gln Val
             20                  25                  30

Val Arg Leu Asp Asp Cys Gly Leu Thr Glu Ala Arg Cys Lys Asp Ile
             35                  40                  45

Ser Ser Ala Leu Arg Val Asn Pro Ala Leu Ala Glu Leu Asn Leu Arg
         50                  55                  60

Ser Asn Glu Leu Gly Asp Val Gly Val His Cys Val Leu Gln Gly Leu
 65                  70                  75                  80

Gln Thr Pro Ser Cys Lys Ile Gln Lys Leu Ser Leu Gln Asn Cys Cys
                 85                  90                  95

Leu Thr Gly Ala Gly Cys Gly Val Leu Ser Ser Thr Leu Arg Thr Leu
                100                 105                 110

Pro Thr Leu Gln Glu Leu His Leu Ser Asp Asn Leu Leu Gly Asp Ala
             115                 120                 125

Gly Leu Gln Leu Leu Cys Glu Gly Leu Leu Asp Pro Gln Cys Arg Leu
         130                 135                 140

Glu Lys Leu Gln Leu Glu Tyr Cys Ser Leu Ser Ala Ala Ser Cys Glu
 145                 150                 155                 160

Pro Leu Ala Ser Val Leu Arg Ala Lys Pro Asp Phe Lys Glu Leu Thr
                 165                 170                 175

Val Ser Asn Asn Asp Ile Asn Glu Ala Gly Val Arg Val Leu Cys Gln
                 180                 185                 190

Gly Leu Lys Asp Ser Pro Cys Gln Leu Glu Ala Leu Lys Leu Glu Ser
             195                 200                 205

Cys Gly Val Thr Ser Asp Asn Cys Arg Asp Leu Cys Gly Ile Val Ala
         210                 215                 220

Ser Lys Ala Ser Leu Arg Glu Leu Ala Leu Gly Ser Asn Lys Leu Gly
 225                 230                 235                 240

Asp Val Gly Met Ala Glu Leu Cys Pro Gly Leu Leu His Pro Ser Ser
                 245                 250                 255

Arg Leu Arg Thr Leu Trp Ile Trp Glu Cys Gly Ile Thr Ala Lys Gly
             260                 265                 270
```

```
Cys Gly Asp Leu Cys Arg Val Leu Arg Ala Lys Glu Ser Leu Lys Glu
            275                 280                 285

Leu Ser Leu Ala Gly Asn Glu Leu Gly Asp Glu Gly Ala Arg Leu Leu
        290                 295                 300

Cys Glu Thr Leu Leu Glu Pro Gly Cys Gln Leu Glu Ser Leu Trp Val
305                 310                 315                 320

Lys Ser Cys Ser Phe Thr Ala Ala Cys Cys Pro His Phe Ser Ser Val
                325                 330                 335

Leu Ala Gln Asn Arg Phe Leu Leu Glu Leu Gln Ile Ser Asn Asn Arg
            340                 345                 350

Leu Glu Asp Ala Gly Val Arg Glu Leu Cys Gln Gly Leu Gly Gln Pro
        355                 360                 365

Gly Ser Val Leu Arg Val Leu Trp Leu Ala Asp Cys Asp Val Ser Asp
370                 375                 380

Ser Ser Cys Ser Ser Leu Ala Ala Thr Leu Leu Ala Asn His Ser Leu
385                 390                 395                 400

Arg Glu Leu Asp Leu Ser Asn Asn Cys Leu Gly Asp Ala Gly Ile Leu
                405                 410                 415

Gln Leu Val Glu Ser Val Arg Gln Pro Gly Cys Leu Leu Glu Gln Leu
            420                 425                 430

Val Leu Tyr Asp Ile Tyr Trp Ser Glu Glu Met Glu Asp Arg Leu Gln
        435                 440                 445

Ala Leu Glu Lys Asp Lys Pro Ser Leu Arg Val Ile Ser
450                 455                 460

(2) INFORMATION FOR SEQ ID NO:7:

(i) SEQUENCE CHARACTERISTICS:
        (A) LENGTH: 1371 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:7:

ATGAACCTGG ACATTCATTG CGAGCAGCTG AGCGACGCCC GGTGGACAGA GCTCCTGCCG      60

CTGCTCCAGC AGTATGAGGT GGTCAGGCTC GACGACTGCG GCCTCACGGA GGAGCACTGC     120

AAGGACATCG GTTCTGCCCT CCGGGCCAAC CCCTCCCTGA CCGAGCTCTG CCTCCGCACC     180

AACGAGCTGG GCGATGCCGG CGTGCACCTG GTGCTGCAGG GCCTGCAGAG CCCCACCTGC     240

AAGATCCAGA AGCTCAGCCT GCAGAACTGC TCCCTGACCG AGGCGGGCTG CGGGGTCCTG     300

CCCAGCACGC TGCGCTCCCT GCCCACGCTG CGGGAGCTGC ATCTCAGCGA CAACCCACTG     360

GGGGACGCCG GCCTGCGGCT GCTCTGTGAG GGGCTCCTGG ACCCCAGTG CCACCTGGAG      420

AAGCTGCAGT TGGAGTACTG CCGCCTGACG GCCGCCAGCT GCGAGCCCCT GGCCTCGGTG     480

CTCAGGGCCA CGCGGGCCTT GAAGGAGCTC ACGGTGAGCA ACAACGACAT CGGCGAGGCC     540

GGCGCCCGGG TGCTGGGCCA GGGTCTGGCC GACTCTGCCT GCCAGCTGGA GACGCTCAGG     600

CTGGAGAACT GCGGTCTCAC GCCAGCCAAC TGCAAAGACC TGTGCGGAAT TGTGGCCTCC     660

CAGGCCTCGC TGCGGGAGCT GGCCCTGGGC AGCAACAAGC TGGGTGATGT GGGCATGGCG     720

GAGCTGTGCC CAGGGCTGCT CCACCCCAGC TCCAGGCTCA GGACCCTGTG GATCTGGGAG     780

TGTGGCATCA CTGCCAAGGG CTGCGGGGAT CTGTGCCGTG TCCTCAGGGC CAAGGAGAGC     840

CTGAAGGAGC TCAGCCTGGC CGGCAACGAG CTGGGGGATG AGGGTGCCCG ACTGCTGTGT     900
```

-continued

```
GAGACCCTGC TGGAACCTGG CTGCCAGCTG GAGTCGCTGT GGGTGAAGTC CTGCAGCTTC      960

ACAGCCGCCT GCTGCCCCCA CTTCAGCTCA GTGCTGGCCC AGAACAGGTT TCTCCTGGAG     1020

CTACAGATAA GCAACAACAG GCTGGAGGAT GCGGGCGTGC GGGAGCTGTG CCAGGGCCTG     1080

GGCCAGCCTG GCTCTGTGCT GCGGGTGCTC TGGTTGGCCG ACTGCGATGT GAGTGACAGC     1140

AGCTGCAGCA GCCTCGCCGC AACCCTGTTG GCCAACCACA GCCTGCGTGA GCTGGACCTC     1200

AGCAACAACT GCCTGGGGGA CGCCGGCATC CTGCAGCTGG TGGAGAGCGT CCGGCAGCCG     1260

GGCTGCCTCC TGGAGCAGCT GGTCCTGTAC GACATTTACT GGTCTGAGGA GATGGAGGAC     1320

CGGCTGCAGG CCCTGGAGAA GGACAAGCCA TCCCTGAGGG TCATCTCCTG A              1371
```

(2) INFORMATION FOR SEQ ID NO:8:

(i) SEQUENCE CHARACTERISTICS:
        (A) LENGTH: 456 amino acids
        (B) TYPE: amino acid
        (C) STRANDEDNESS: both
        (D) TOPOLOGY: both (ii) MOLECULE TYPE: peptide (xi) SEQUENCE DESCRIPTION: SEQ ID NO:8:

```
Met Asn Leu Asp Ile His Cys Glu Gln Leu Ser Asp Ala Arg Trp Thr
1               5                   10                  15

Glu Leu Leu Pro Leu Leu Gln Gln Tyr Glu Val Val Arg Leu Asp Asp
            20                  25                  30

Cys Gly Leu Thr Glu Glu His Cys Lys Asp Ile Gly Ser Ala Leu Arg
        35                  40                  45

Ala Asn Pro Ser Leu Thr Glu Leu Cys Leu Arg Thr Asn Glu Leu Gly
    50                  55                  60

Asp Ala Gly Val His Leu Val Leu Gln Gly Leu Gln Ser Pro Thr Cys
65                  70                  75                  80

Lys Ile Gln Lys Leu Ser Leu Gln Asn Cys Ser Leu Thr Glu Ala Gly
                85                  90                  95

Cys Gly Val Leu Pro Ser Thr Leu Arg Ser Leu Pro Thr Leu Arg Glu
            100                 105                 110

Leu His Leu Ser Asp Asn Pro Leu Gly Asp Ala Gly Leu Arg Leu Leu
        115                 120                 125

Cys Glu Gly Leu Leu Asp Pro Gln Cys His Leu Glu Lys Leu Gln Leu
    130                 135                 140

Glu Tyr Cys Arg Leu Thr Ala Ala Ser Cys Glu Pro Leu Ala Ser Val
145                 150                 155                 160

Leu Arg Ala Thr Arg Ala Leu Lys Glu Leu Thr Val Ser Asn Asn Asp
                165                 170                 175

Ile Gly Glu Ala Gly Ala Arg Val Leu Gly Gln Gly Leu Ala Asp Ser
            180                 185                 190

Ala Cys Gln Leu Glu Thr Leu Arg Leu Glu Asn Cys Gly Leu Thr Pro
        195                 200                 205

Ala Asn Cys Lys Asp Leu Cys Gly Ile Val Ala Ser Gln Ala Ser Leu
    210                 215                 220

Arg Glu Leu Ala Leu Gly Ser Asn Lys Leu Gly Asp Val Gly Met Ala
225                 230                 235                 240

Glu Leu Cys Pro Gly Leu Leu His Pro Ser Ser Arg Leu Arg Thr Leu
                245                 250                 255

Trp Ile Trp Glu Cys Gly Ile Thr Ala Lys Gly Cys Gly Asp Leu Cys
            260                 265                 270
```

```
Arg Val Leu Arg Ala Lys Glu Ser Leu Lys Glu Leu Ser Leu Ala Gly
            275                 280                 285

Asn Glu Leu Gly Asp Glu Gly Ala Arg Leu Leu Cys Glu Thr Leu Leu
            290                 295                 300

Glu Pro Gly Cys Gln Leu Glu Ser Leu Trp Val Lys Ser Cys Ser Phe
305                 310                 315                 320

Thr Ala Ala Cys Cys Pro His Phe Ser Ser Val Leu Ala Gln Asn Arg
                325                 330                 335

Phe Leu Leu Glu Leu Gln Ile Ser Asn Asn Arg Leu Glu Asp Ala Gly
            340                 345                 350

Val Arg Glu Leu Cys Gln Gly Leu Gly Gln Pro Gly Ser Val Leu Arg
            355                 360                 365

Val Leu Trp Leu Ala Asp Cys Asp Val Ser Asp Ser Cys Ser Ser
370                 375                 380

Leu Ala Ala Thr Leu Leu Ala Asn His Ser Leu Arg Glu Leu Asp Leu
385                 390                 395                 400

Ser Asn Asn Cys Leu Gly Asp Ala Gly Ile Leu Gln Leu Val Glu Ser
                405                 410                 415

Val Arg Gln Pro Gly Cys Leu Leu Glu Gln Leu Val Leu Tyr Asp Ile
            420                 425                 430

Tyr Trp Ser Glu Glu Met Glu Asp Arg Leu Gln Ala Leu Glu Lys Asp
            435                 440                 445

Lys Pro Ser Leu Arg Val Ile Ser
            450                 455

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

TAATAGCATA TGAGTCTTGA CATCCAGTGT GAG                                33

(2) INFORMATION FOR SEQ ID NO:10:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

TTATTAGGAT CCTTATCAGG AAATGATCCT CAGGGATGGC C                       41

(2) INFORMATION FOR SEQ ID NO:11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

TATTATCATA TGAACCTSGA YATYCAYTGY GA                                 32
```

(2) INFORMATION FOR SEQ ID NO:12:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

TATTATAAGC TTGCCCAAAA GGTGTTTTAC TAAGTAG                    37

(2) INFORMATION FOR SEQ ID NO:13:

(i) SEQUENCE CHARACTERISTICS:
        (A) LENGTH: 35 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:13:

TATTATCATA TGAGCCTGGA CATCCAGAGC CTGGA                      35

(2) INFORMATION FOR SEQ ID NO:14:

(i) SEQUENCE CHARACTERISTICS:
        (A) LENGTH: 39 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:14:

TATTAGAATT CAAGCTTATC AGGAGATGAC CCTCAGGGA                  39

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:15:

GTGGCCTCCA AGGCCTCGCT GCGG                                  24

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:16:

CCGCAGCGAG GCCTTGGAGG CCAC                                  24

MAMMALIAN RIBONUCLEASE INHIBITORS AND USE THEREOF

CROSS-REFERENCE TO RELATED APPLICATIONS

This application is a continuation-in-part of U.S. application Ser. No. 08/795,395, filed Feb. 4, 1997, which is a continuation-in-part of U.S. application Ser. No. 08/794,546, filed Feb. 3, 1997, now abandoned, which claims priority to U.S. Provisional Application No. 60/024,057, filed Aug. 16, 1996. The contents of each of these patent applications are fully incorporated by reference herein.

FIELD OF THE INVENTION

The present invention is in the fields of molecular biology and protein chemistry. The invention relates to the successful cloning of a fill length cDNA of porcine liver ribonuclease inhibitor (RI) gene and its expression in a cellular host. In addition, the invention relates to the cloning of full length rat liver RI, and its expression in a cellular host. The invention also relates to the successful cloning of full length human liver RI, and to the cloning of chimeric mammalian RIs, particularly a chimeric porcine/human RI, which demonstrate increased thermostability relative to non-human RIs.

BACKGROUND OF THE INVENTION

RI is a cytoplasmic protein ubiquitously present in a variety of mammalian tissues. It inhibits a variety of ribonucleases (RNases) by binding tightly to both intracellular and extracellular RNases by forming a 1:1 complex (Roth, J. S., *Methods Cancer Res.* 3: 153–243 (1967); Blackburn, P., et al., *J Biol. Chem.* 252: 5904–5910 (1977); Blackburn, P., *J. Biol. Chem.* 254: 12484–12487 (1979); Blackburn, P., and Moore, S., *Enzymes,* 3rd Ed. (1982), vol. 15, pp. 317–433; Lee, F. S., et al., *Biochemistry* 27: 8545–8553 (1988)). Some evidence indicates that tissues which are highly active in protein synthesis have a high excess of RI over RNase. Conversely, in catabolically active tissues that do not accumulate RNA, the ratio of RI to RNase is low (Kraft, N., and Shortman, K., *Biochim. Biophys. Acta.* 217: 164–175 (1970)). The biological function of RI has been implicated to be in (a) regulation of RNA turnover by controlling cytoplasmic RNase activity, (b) safeguarding against non-cytoplasmic RNases that mislocalized to the cytoplasm, and (c) regulation of angiogenin, a protein that induces blood vessel growth and contains RNase activity. In vitro, RI is useful in a variety of molecular biology applications where RNase contamination is a potential problem. Examples of these applications include reverse transcription of mRNA, cell-free translation systems, preparation of RNase-free antibodies, and it vitro virus replication. Ideally, RI to be used in these kinds of applications will be capable of inhibiting a large number of RNases, such as eukaryotic RNase A, RNase B and RNase C, as well as prokaryotic RNases.

RI has been purified to homogeneity from several mammalian tissues, including placenta (Blackburn, P., et al., *J Biol. Chem.* 252: 5904–5910 (1977); Blackburn, P., *J Biol. Chem.* 254: 12484–12487 (1979)), brain (Burton, L. E., et al, *Int. J. Pept. Protein Res.* 16: 359–364 (1980)) and liver (Burton, L. E., and Fucci, N. P., *Int. J Pept. Protein Res.* 18: 372–379 (1982); Hofsteenge, J., et al., *Biochemistry* 27: 8537–8544 (1988)). The protein has an apparent molecular mass of approximately 50 kilodaltons (kD). The primary amino acid sequence of various RIs, such as human placental (Lee, F. S., et al, *Biochemistry* 27: 8545–8553 (1988)), porcine liver (Hofsteenge, J., et al., *Biochemisitry* 27: 8537–8544 (1988)) and rat lung (Kawanomoto, M., et al., *Biochim. Biophys. Acta.* 1129: 335–338 (1992)) is known. The crystal structure of porcine RI has been published (Kobe, B., and Deisenhofer, J., *Nature* 366: 751–756 (1993)). The human placental RI has been successfully cloned and expressed in *E. coli* (Lee, F. S., et al., *Biochemistry* 27: 8545–8553 (1988); Promega Catalog 1993/1994). A complete rat lung RI cDNA has been described (Kawanomoto et al., *Biochim. Biophys. Acta.* 1129: 335–338 (1992)); this cDNA has been used to study the distribution of the RI mRNA in various tissues.

The complete coding sequence of rat lung RI is known, but recombinant rat lung RI has not been expressed in either *E. coli* or any other known expression host (Kawanomoto, M., el al., *Biochim. Biophys. Acta* 1129: 335–338 (1992)). Several attempts to isolate a cDNA clone for rat liver RI have similarly been unsuccessful (Id).

The complete amino acid sequence of porcine RI has been determined by direct sequencing of the purified protein. In addition, a partial cDNA sequence of porcine kidney RI has been described by Vicentini, A. M., et al. (*Biochemistry* 29: 8827–8834 (1990)). The cDNA lacks 241 nucleotides at the 5'-end of the coding sequence corresponding to the first 81 amino acids of porcine kidney RI. However, a synthetic complete porcine kidney RI coding sequence has been prepared by ligating a synthetic oligonucleotide encoding amino acid residues 1–81 of porcine RI, the sequence of which is based on the amino acid sequence of porcine liver RI, to a restriction fragment of the incomplete cDNA which corresponds to amino acid residues 82–456 of the above-mentioned cDNA. This protein has been expressed in *Saccharomyces cerevisiace.*

From the foregoing, it will be clear that there is a need in the art for recombinantly produced RNase inhibitors that are active against a broad range of RNases from both eukaryotic and prokaryotic sources.

BRIEF SUMMARY OF THE INVENTION

The invention relates to the successful cloning of a full length cDNA of porcine liver RI gene and its expression in a cellular host.

More particularly, the invention relates to a composition comprising an isolated nucleic acid molecule comprising a nucleotide sequence (SEQ ID NO:1) encoding the complete coding sequence of porcine ribonuclease inhibitor (RI). In another embodiment, this nucleic acid molecule is operably linked to a promoter for expression of porcine RI. In another embodiment, the invention relates to a vector comprising this latter construct, which when introduced into a cellular host leads to expression of porcine RI. In another embodiment, the invention relates to a host cell comprising the above-described vector and to recombinant hosts comprising the porcine RI sequence. The invention also relates to a method of obtaining a porcine RI polypeptide (such as that depicted in SEQ ID NO:2), comprising obtaining the host cell or recombinant host described above and isolating a porcine RI polypeptide from it.

The invention also relates to the cloning of a cDNA encoding rat liver RI, and its expression in a cellular host.

More particularly, the invention relates to a composition comprising an isolated nucleic acid molecule comprising a nucleotide sequence encoding the complete coding sequence of rat liver RI (SEQ ID NO:3). The invention also relates to a molecule wherein the coding sequence is operably linked to a promoter for expression of rat liver RI. In another embodiment, the invention relates to a vector comprising the above described nucleic acid molecule which, when introduced into a cellular host, leads to expression of rat liver RI. In another embodiment, the invention relates to a host cell transformed with the above described vector and to recombinant hosts containing the rat RI sequence. The invention also relates to a method for obtaining a rat liver RI polypeptide (such as that depicted in SEQ ID NO:4), comprising culturing this host cell or recombinant host and isolating a rat liver RI polypeptide from it.

The invention also relates to isolated nucleic acid molecules comprising a polynucleotide encoding a human liver RI. The invention also relates to molecules in which the human liver RI sequence is operably linked to a promoter for expression of human liver RI. Preferred nucleic acid molecules include those wherein the polynucleotide encoding the human liver RI has a nucleotide sequence at least 99% identical to a reference sequence selected from the group consisting of (a) the nucleotide sequence set forth in SEQ ID NO:5, wherein T can also be U; (b) a nucleotide sequence encoding the human liver RI polypeptide having the complete amino acid sequence encoded by the cDNA clone contained in NRRL Deposit No. B-21810; and (c) a nucleic acid sequence complementary to (a) or (b). The invention also relates to isolated nucleic acid molecules comprising a polynucleotide which hybridizes under stringent hybridization conditions to a polynucleotide having a nucleotide sequence identical to the nucleotide sequence of the above-described nucleic acid molecules. The invention also relates to vectors comprising the human liver RI sequence, to host cells comprising such vectors, and to recombinant hosts comprising human liver RI sequences. The invention also relates to methods for producing a human liver RI polypeptide (such as that depicted in SEQ ID NO:6), the methods comprising culturing the host cells or recombinant hosts of the invention and isolating a human liver RI polypeptide. The invention also relates to a human liver RI polypeptide produced according to these methods.

In another embodiment, the invention relates to isolated nucleic acid molecules comprising a polynucleotide encoding a chimeric mammalian RI, which may be thermostable, wherein the polynucleotide comprises a substantial portion of a nucleotide sequence encoding a RI from a first mammalian species (preferably a non-human species such as porcine, rat, equine, bovine, ovine, murine, canine, feline, ape, monkey, etc.) and a substantial portion of a nucleotide sequence encoding a RI from a second mammalian species which is different from the first mammalian species (preferably a human, the polynucleotide preferably encoding a human liver RI or a human placental RI). The invention also relates to molecules in which the chimeric RI sequence is operably linked to a promoter for expression of the chimeric RI. Nucleic acid molecules according to the invention may include those comprising a polynucleotide encoding a chimeric porcine/human RI, such as those wherein the polynucleotide encoding the chimeric mammalian RI has a nucleotide sequence at least 90% or at least 95% identical to a reference sequence selected from the group consisting of: (a) the nucleotide sequence set forth in SEQ ID NO:7, wherein T can also be U, and (b) a nucleic acid sequence complementary to (a). The invention also relates to isolated nucleic acid molecules comprising a polynucleotide which hybridizes under stringent hybridization conditions to a polynucleotide having a nucleotide sequence identical to the nucleotide sequence of the above-described nucleic acid molecules. The invention also relates to vectors containing chimeric RI sequences, to host cells comprising such vectors, and to recombinant hosts containing the chimeric RI sequences.

The invention also relates to methods for producing a chimeric mammalian RI polypeptide, which may be thermostable, the methods comprising culturing the host cells of the invention and isolating a chimeric mammalian RI polypeptide. The invention also relates to a chimeric mammalian RI polypeptide produced according to these methods, which may be a chimeric porcine/human RI polypeptide (such as that depicted in SEQ ID NO:8) and which may be thermostable.

The invention also relates to any of the described nucleic acid molecules which may further comprise one or more nucleotide sequences encoding one or more binding peptides. Such sequences encoding binding peptides may be located 5' to the translation start site of the polynucleotide encoding the RI or chimeric RI. Binding peptides according to this aspect of the invention may include an OmpA signal sequence, a GST tag, a HIS tag, a thioredoxin tag or a hemagglutinin (HA) tag. Vectors containing these modified molecules, host cells comprising such vectors and recombinant hosts containing these modified molecules are also contemplated by the invention.

In another aspect, the invention relates to methods for producing a nucleic acid molecule comprising mixing a template nucleic acid molecule, which may be an RNA molecule such as a mRNA or polyA+RNA molecule, with one or more of the RI polypeptides of the invention (preferably chimeric RI such as a chimeric porcine/human RI polypeptide) under conditions sufficient to synthesize a nucleic acid molecule from the template molecule. According to this aspect of the invention, the mixture may further comprise one or more thermostable DNA polymerases such as Tne, Tma, Taq, Pfu, Tth, Tfi, VENT, DEEPVENT, Pwo or Tfl polymerases, or mutants, variants and derivatives thereof. The mixtures may also comprise one or more polypeptides having reverse transcriptase activity, such as M-MLV reverse transcriptase, RSV reverse transcriptase, AMV reverse transcriptase, RAV reverse transcriptase, MAV reverse transcriptase or HIV reverse transcriptase. These polypeptides having reverse transcriptase activity may be substantially reduced in RNase H activity; preferred such polypeptides include M-MLV H⁻ reverse transcriptase, RSV H⁻ reverse transcriptase, AMV H⁻ reverse transcriptase, RAV H⁻ reverse transcriptase, MAV H⁻ reverse transcriptase and HIV H⁻ reverse transcriptase. The mixtures used in these methods may also optionally comprise one or more polypeptides having RNA polymerase activity. According to the invention, the methods for producing a nucleic acid molecule may be performed at temperatures of from about 45° C. to about 70° C., from about 50° C. to about 65° C., from about 55° C. to about 60° C., from about 56° C. to about 60° C., from about 57° C. to about 60° C., from about 58° C. to about 60° C., from about 59° C. to about 60° C., or at a temperature of 50° C. or greater, 51° C. or greater, 52° C. or greater, 53° C. or greater, 54° C. or greater, 55° C. or greater, 56° C. or greater, 57° C. or greater, 58° C. or greater, 59° C. or greater, 60° C. or greater, 61° C. or greater, 62° C. or greater, 63° C. or greater, 64° C. or greater or 65° C. or greater.

The invention also relates to nucleic acid molecules produced according to these methods, which may be DNA molecules (including cDNA molecules), RNA molecules or DNA-RNA hybrid molecules, and which may be single-stranded or double-stranded.

In another aspect, the invention relates to methods for ini vitro production of a polypeptide comprising mixing a mRNA or polyA+RNA molecule with one or more of the RIs of the invention (such as a porcine liver, rat liver, human liver or chimeric mammalian (particularly a chimeric porcine/human) RI polypeptide), under conditions sufficient to translate a polypeptide from the MRNA or polyA+RNA molecule. The invention also relates to polypeptides produced according to these methods.

The invention is also directed to kits comprising one or more containers containing one or more of the above-described RIs of the invention. Kits according to this aspect of the invention may further comprise additional containers containing, for example, one or more of the thermostable DNA polymerases, polypeptides having reverse transcriptase activity or polypeptides having RNA polymerase activity described above. Additional kits of the invention may further comprise one or more containers containing a cell-free protein translation mixture.

Other preferred embodiments of the present invention will be apparent to one of ordinary skill in light of the following drawings and description of the invention, and of the claims.

DETAILED DESCRIPTION OF THE INVENTION

Definitions

Figure 1:
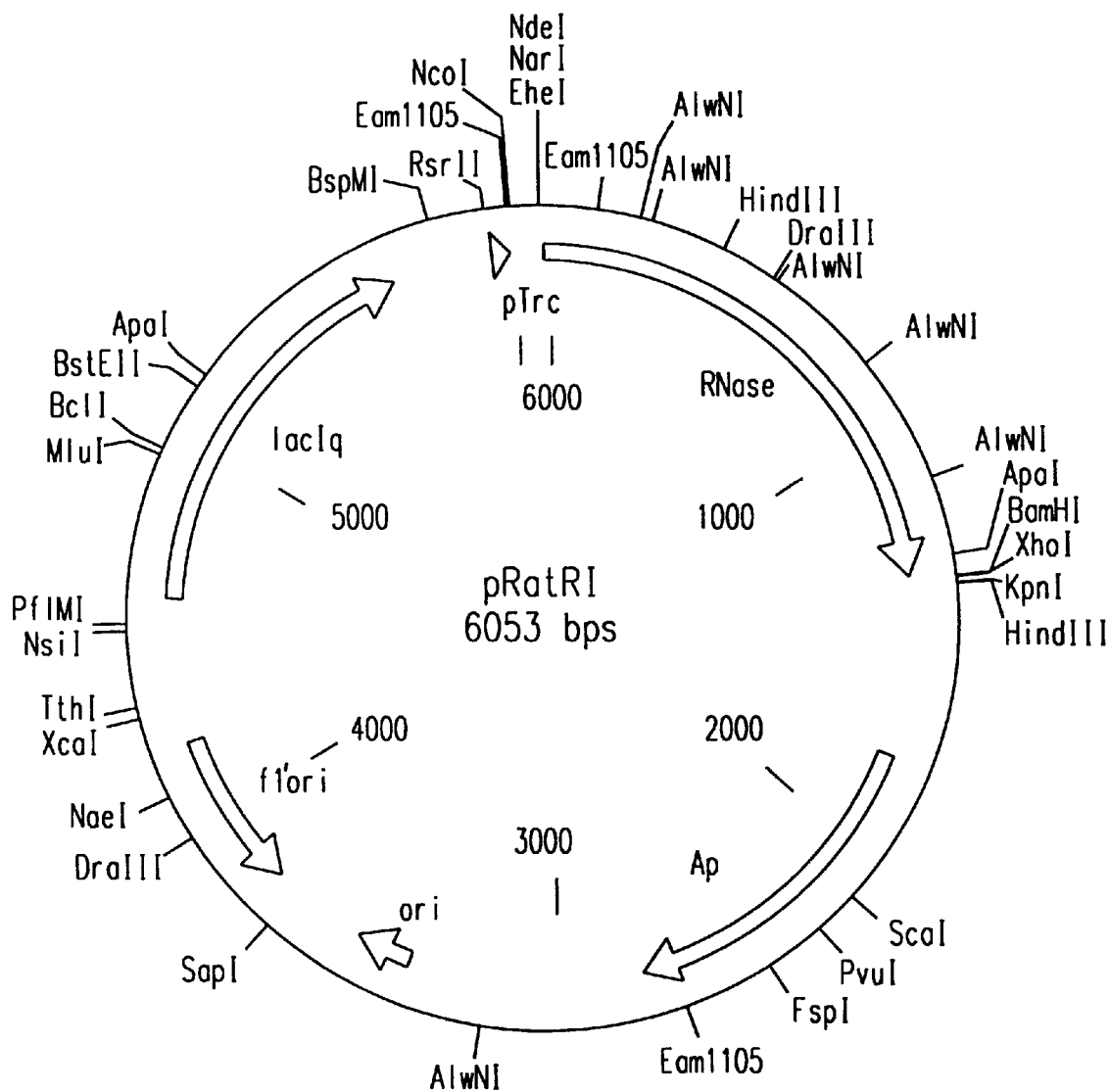
FIG. 1 is a map of plasmid pRatRI.

In the description that follows, a number of terms used in recombinant DNA technology are utilized extensively. In order to provide a clear and consistent understanding of the specification and claims, including the scope to be given such terms, the following definitions are provided.

Cloning vector. A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

Expression vector. A vector similar to a cloning vector but which is capable of expressing a gene which has been cloned into it, after transformation into a host. The cloned gene is usually placed under the control of (i. e., operably linked to) certain control sequences such as promoter sequences. Promoter sequences may be either constitutive, repressible or inducible.

Substantially pure. As used herein, this term means that the desired purified protein is free from contaminating cellular components which would substantially inhibit the ribonuclease inhibiting activity of the protein. For example, a "substantially purified" or "substantially pure" RI means a preparation of RI polypeptide wherein at least 50%, preferably at least 70%, and more preferably at least 80%, 85%, 90%, 91%, 92%, 93%, 94%, 95%, 96%, 97%, 98% or 99% of contaminating proteins (i.e., those that are not RI proteins) have been removed from the preparation. "Substantially pure" does not indicate that the protein must be completely free of all contaminants.

Substantially RNase Free. The terms "substantially RNase free" and "substantially free of RNase" are defined herein as having less than 10%, preferably about or less than 1% and most preferably about or less than 0.1%, of the RNase activity found when purifying ribonuclease inhibitor with an RNase affinity column. For assays to determine RNase activity and ribonuclease inhibitor activity, see Goldman et al., *Prep. Biochem.* 11: 49–67 (1981).

Recombinant Host. According to the invention, a recombinant host may be any prokaryotic or eukaryotic microorganism which contains the desired cloned genes on an expression vector or cloning vector. This term is also meant to include those microorganisms that have been genetically engineered to contain the desired gene(s) in the chromosome or genome of that organism.

Recombinant vector. Any cloning vector or expression vector which contains the desired cloned gene(s).

Host Any prokaryotic or eukaryotic microorganism that is the recipient of a replicable expression vector or cloning vector. A "host," as the term is used herein, also includes prokaryotic or eukaryotic microorganisms that can be genetically engineered by well known techniques to contain desired gene(s) on its chromosome or genome. For examples of such hosts, see Maniatis et al., *Molecular Cloning: A Laboratory Manual*, Cold Spring Harbor Laboratory, Cold Spring Harbor, N.Y. (1982).

Promoter. A DNA sequence generally described as the 5' region of a gene, located proximal to the start codon. The transcription of an adjacent gene(s) is initiated at the promoter region. Promoters can be inducible, repressible or constitutive. Genes that are under the control of an inducible or repressible promoter are transcribed at levels that vary in response to the external environment. If a promoter is an inducible promoter, then the rate of transcription increases in response to an inducing agent. If a promoter is a repressible promoter, then the rate of transcription decreases in response to repressor (or negative regulator). It is possible for a promoter to be both inducible and repressible. Transcription from such a promoter will be inhibited in response to a repressor; this inhibition may be reversed by the action of an inducing agent. An example of such a promoter that is well known by those of ordinary skill in the art is the lac promoter. A description of the regulation of the lac promoter may be found in Lewin, Genes V, Oxford University Press, N.Y. (1994). In contrast, if the promoter is a constitutive promoter, the rate of transcription is not regulated by the external environment.

Repression. Repression is the inhibition of transcription effected by the binding of repressor protein to a specific site on DNA.

Induction. Induction is the switching on of transcription as a result of interaction of an inducer with a positive or negative regulator.

Positive Regulation of Transcription. A mechanism of control of gene expression where a gene is not transcribed unless a positive regulator, or activator, allows initiation of transcription.

Negative Regulation of Transcription. A mechanism of control of gene expression where a gene is transcribed unless transcription is prevented by the action of a negative regulator, or repressor.

Repressor. A protein which prevents transcription by binding to a specific site on DNA.

Operator. The site on DNA at which a repressor protein binds to prevent transcription from initiating at the adjacent promoter.

Inducer. A molecule that triggers gene transcription by binding to a regulator protein such as a repressor.

Gene. A DNA sequence that contains information needed for expressing a polypeptide or protein.

Structural gene. A DNA sequence that is transcribed into messenger RNA (mRNA) that is then translated into a sequence of amino acids characteristic of a specific polypeptide.

Expression. Expression is the process by which a polypeptide is produced from a structural gene. The process involves transcription of the gene into mRNA and the translation of such mRNA into polypeptide(s).

Chimeric. A chimeric molecule is a molecule that is composed of a portion of a molecule obtained from one species of organism fused or otherwise joined to a portion of a molecule obtained from another species of organism. For example, a chimeric porcine/human enzyme may be made by linking, usually using genetic engineering techniques, one or more portions of the porcine form of the enzyme to one or more portions of the human form of the enzyme. Analogously, a chimeric porcine/human polynucleotide may be made by linking one or more portions of the porcine form of a polynucleotide (e.g., a polypeptide-encoding gene) to one or more portions of the human form of the polynucleotide. Chimeric polypeptides may then be obtained by transfecting a host cell with one or more of these chimeric polynucleotides and culturing the host cells under conditions favoring the expression of the chimeric polynucleotides by the host cells.

Nucleic Acid Molecules and Polypeptides

Porcine and Rat Liver RIs

The invention relates to a composition comprising an isolated nucleic acid molecule comprising a nucleotide sequence encoding the complete coding sequence of porcine ribonuclease inhibitor (RI).

The invention also relates to a composition comprising an isolated nucleic acid molecule comprising a nucleotide sequence encoding the complete coding sequence of rat ribonuclease inhibitor (RI).

In a preferred embodiment, a sequence encoding either rat or porcine RI is operably linked to a promoter for expression of the RI protein. In another preferred embodiment, a sequence encoding either rat liver or porcine liver RI is operably linked to a promoter for expression of the RI protein.

In another preferred embodiment, the invention relates to a composition comprising an isolated nucleic acid molecule comprising a nucleotide sequence of porcine liver RI, wherein said nucleotide sequence is selected from the group consisting of:

(a) the sequence set forth in SEQ ID NO:1, wherein T can also be U;

(b) a nucleotide sequence encoding the porcine RI polypeptide having the complete amino acid sequence encoded by the cDNA clone contained in NRRL Deposit No. B-21612;

(c) a nucleotide sequence complementary to (a) or (b); and (d) fragments of (a) or (b) or (c) which fall within a portion of SEQ ID NO:1, wherein said fragments are at least 18 bases in length, and will hybridize to porcine genomic DNA encoding liver RI under stringent hybridization conditions. Preferably, the fragments fall within the portion of SEQ ID NO:1 that encodes the first 81 amino acids of porcine liver RI.

In another preferred embodiment, the invention relates to a composition comprising an isolated nucleic acid molecule comprising a nucleotide sequence of rat liver RI, wherein said nucleotide sequence is selected from the group consisting of:

(a) the sequence set forth in SEQ ID NO:3, wherein T can also be U;

(b) a nucleotide sequence encoding the rat RI polypeptide having the complete amino acid sequence encoded by the cDNA clone contained in NRRL Deposit No. B-21613;

(c) a nucleotide sequence complementary to (a) or (b); and (d) fragments of (a), (b) or (c) which fall within a portion of SEQ ID NO:3, wherein said fragments are at least 18 bases in length, and will hybridize to rat RI under stringent hybridization conditions.

By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 $\mu$g/ml denatured, sheared salmon sperm DNA, followed by washing the filters in 0.1×SSC at about 65° C.

Such nucleic acid molecules and fragments thereof are useful as DNA probes for detecting expression of RI in porcine or rat tissue by northern blot analysis, or as primers for amplification of a target sequence by the polymerase chain reaction (PCR).

Since the nucleotide sequences of porcine and rat liver RI are provided, generating such DNA fragments would be routine to the skilled artisan. For example, restriction endonuclease cleavage or shearing by sonication could easily be used to generate fragments of various sizes. Alternatively, the DNA fragments of the present invention could be generated synthetically according to known techniques.

The present invention also relates to vectors which include the isolated DNA molecules of the present invention, host cells which are genetically engineered with the recombinant vectors, and the production of porcine liver or rat liver RI polypeptides (such as those depicted in SEQ ID NOs:2 and 4, respectively) by recombinant techniques.

Eukaryotic and prokaryotic hosts that may be used for cloning and expressing the enzymes of the invention are well known in the art. Vectors which replicate in such host cells are also well known. The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; ptrc99a, pKK223-3, pKK233-3, pDR540, pRIT5 available from Pharmacia; and pUC18, pUC19 and pPROEX1, available from Life Technologies, Inc. (LTI; Rockville, Md.). Among preferred eukaryotic vectors are pWLNEO, pSV2CAT, pOG44, pXT1 and pSG available from Stratagene; and pSVK3, pBPV, pMSG and pSVL available from Pharmacia (Piscataway, N.J.). These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Preferred prokaryotic hosts include, but are not limited to, bacteria of the genus Escherichia, Bacillus, Streptomyces, Pseudomonas, Salmonella, Serratia, Xanththomonas, etc. Two of the most preferred prokaryotic hosts are *E. coli* DH10B and DH5αF'IQ (available from LTI).

Host cells can be genetically engineered to incorporate nucleic acid molecules and express polypeptides of the present invention. For instance, recombinant constructs may be introduced into host cells using well known techniques of infection, transduction, transfection, and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate, polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited above, which is illustrative of the many laboratory manuals that detail these techniques.

In accordance with this aspect of the invention the vector may be, for example, a plasmid vector, a single or double-stranded phage vector, or a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsulated virus by well known techniques for infection and transduction. Viral vectors may be replication competent or replication defective. In the latter case viral propagation generally will occur only in complementing host cells.

The present invention also encompasses the expression of rat liver or porcine liver RI in prokaryotic and eukaryotic cells. Therefore, preferred among vectors, in certain respects, are those for expression of the polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

In order to express the porcine or rat RI polypeptides of the invention, the polynucleotides encoding these genes generally will be inserted into the vector using standard techniques so that they are operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional coding sequence which codes for additional amino acids, such as those which provide additional functionalities. Thus, for instance, the polypeptide may be fused to a tag sequence, such as a peptide or leader peptide, which facilitates purification of the fused polypeptide. In certain preferred embodiments of this aspect of the invention, the marker sequence is a hexa-histidine peptide, such as the tag provided in the pPROEX1 vector (LTI), among others, many of which are commercially available. As described in Gentz ef al., *Proc. Natl. Acad. Sci., USA* 86: 821–824 (1989), for instance, hexa-histidine provides for convenient purification of the fusion protein. The polypeptide may also be fused to the (hemagglutinin) HA tag, which corresponds to an epitope derived of influenza hemagglutinin protein, described by Wilson et al., *Cell* 37: 767 (1984), for instance. The fusion of the HA tag to the target protein allows easy detection or isolation of the recombinant protein with an antibody that recognizes the HA epitope. The sequence encoding the target protein may also be fused with sequence encoding the outer membrane protein A (OmpA) signal secretion sequence (21 amino acids) (Humphreys, D. P., et al., *J. Biol. Chem.* 270: 28210–28215 (1995). Other tags that may be used for this purpose include the glutathione S-transferase (GST) tag and the thioredoxin tag (Chopra, A. K., et al., *Gene (Amsterdam*) 144: 81–85 (1994). Thus, for instance, a region of additional amino acids, particularly charged amino acids, may be added to the N-terminus of the polypeptide to improve stability and persistence in the host cell, during purification or during subsequent handling and storage. Also, regions may be added to the polypeptide to facilitate enhanced expression as well as purification. Such regions may be removed prior to final preparation of the polypeptide. The addition of peptide moieties to polypeptides to engender secretion or excretion, to improve stability and to facilitate purification, among others, are familiar and routine techniques in the art.

The DNA molecule inserted in the expression vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. It will be understood that numerous promoters not mentioned are suitable for use in this aspect of the invention are well known and readily may be employed by those of skill in the manner illustrated by the discussion and the examples herein. Polynucleotides of the invention, encoding the polypeptides of the invention, generally will be inserted into the vector using standard techniques so that they are operably linked to the promoter for expression. The polynucleotide will be positioned so that the transcription start site is located appropriately 5' to a ribosoine binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing *E. coli* and other bacteria.

Hosts for of a great variety of expression constructs are well known, and those of skill will be enabled by the present disclosure readily to select a host for expressing a polypeptides in accordance with this aspect of the present invention.

Selection of appropriate vectors and promoters for expression in a host cell is a well known procedure and the requisite techniques for expression vector construction, introduction of the vector into the host and expression in the host are routine skills in the art.

Following transformation of a suitable host strain and growth of the host strain to an appropriate cell density, where the selected promoter is inducible, expression of the RI of the invention is induced by appropriate means (e.g., temperature shift or exposure to chemical inducer) and cells are cultured for an additional period.

In a preferred embodiment, the plasmid pPROEX1 is used for the expression of either rat or porcine RI. pPROEX1 contains the gene for the lacI$^q$ repressor, which blocks expression of the inserted gene of interest (here, the gene encoding porcine or rat RI) by binding to the lac operator unless an inducer such as isopropylthiogalactoside (IPTG) is present.

Of course, it will be understood by those of skill in the art that other inducers besides IPTG can be utilized where the RI gene is under the control of a lacI$^q$-repressible promoter, including but not limited to other thiogalactosides.

Where porcine RI is to be expressed, it is particularly preferred that the host cell expressing the porcine RI be a cell that constitutively expresses the repressor which controls porcine RI expression (see Example 2). Therefore, a particularly preferred method of expressing porcine RI comprises transforming a vector, which comprises the gene encoding porcine RI under the control of the lac promoter, into a host cell which constitutively expresses the lac repressor, and then inducing expression of porcine RI after the cells have grown to a sufficient density, such as an A590 of between about 0.6 and 1.0.

It will thus be understood by those of ordinary skill that other expression systems may be utilized, so long as the expression of porcine liver RI is tightly controlled. In such an expression system, the host cell harboring the porcine RI gene can be grown to a desired cell density, at which point expression of porcine RI can be initiated.

In order to obtain the RI, cells typically are then harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents; such methods are well know to those skilled in the art.

The rat liver RI or porcine liver RI polypeptide can be recovered and purified from recombinant cell cultures by well-known methods including ammonium sulfate precipitation, anion or cation exchange chromatography, phosphocellulose chromatography, hydrophobic interaction chromatography, affinity chromatography, hydroxyapatite chromatography and lectin chromatography. Most preferably, affinity chromatography is employed for purification. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Human Liier RIs and Chimeric Mammalian RIs

The invention also relates to nucleic acid molecules, vectors, host cells and recombinant hosts comprising human liver and chimeric RIs. The description above related to vectors, cloning, expression, protein purification, etc., also apply equally to the human and chimeric RI's of the invention. Specifically, using the techniques described in more detail below in Example 7, the invention relates to a full-length cDNA clone of human liver RI. Also provided by the present invention, as described in detail below in Example 8, are chimeric mammalian RIs comprising a substantial portion of a RI polypeptide from a first mammalian species linked to a substantial portion of a RI polypeptide from a second mammalian species.

Thus, the invention relates to isolated nucleic acid molecules comprising a polynucleotide encoding a human liver RI. Preferred nucleic acid molecules include those wherein the polynucleotide encoding the human liver RI has a nucleotide sequence at least 90%, preferably at least 95% and most preferably at least about 99%, identical to a reference sequence selected from the group consisting of (a) the nucleotide sequence set forth in SEQ ID NO:5, wherein T can also be U; (b) a nucleotide sequence encoding the human liver RI polypeptide having the complete amino acid sequence encoded by the cDNA clone contained in NRRL Deposit No. B-21810; and (c) a nucleic acid sequence complementary to (a) or (b). Such isolated molecules, particularly DNA molecules, are useful as probes for gene mapping by in situ hybridization with chromosomes, for detecting expression of the human liver RI gene in tissue samples, and for the production of human liver RI, among other uses detailed below.

In addition, the invention provides isolated nucleic acid molecules comprising a polynucleotide encoding a chimeric mammalian RI, particularly wherein the polynucleotide comprises a substantial portion of a nucleotide sequence encoding a RI from a first mammalian species and a substantial portion of a nucleotide sequence encoding a RI from a second mammalian species which is different from the first mammalian species. As used herein, the term "a substantial portion of a nucleotide sequence" means at least 100 contiguous nucleotides, at least 150 contiguous nucleotides, at least 200 contiguous nucleotides or at least 250–500 contiguous nucleotides, of a nucleotide sequence encoding a given RI. According to the invention, the first mammalian species is preferably non-human and the second mammalian species is preferably human, although nucleic acid molecules in which both mammalian species are non-human (but which are different from each other) are also intended to be encompassed by the invention. Examples of such nucleic acid molecules include, but are not limited to, those encoding a porcine/human RI, a rat/human RI, a murine/human RI, a bovine/human RI, an equine/human RI, an ovine/human RI, a canine/human RI, a feline/human RI, an ape/human RI, a monkey/human RI, etc. In a particularly preferred embodiment, the polynucleotide or portion thereof encoding a human RI encodes a human liver RI (SEQ ID NO:5) or a human placental RI (Lee, F. S., etal., *Biochemistry* 27: 8545–8553 (1988)).

It has unexpectedly been found in the present invention that chimeric mammalian RIs comprising a portion (e.g., the carboxy terminal portion) of a human RI, such as a human liver or placental RI, makes the RI thermostable. By a "thermostable RI" is intended a RI polypeptide or fragment thereof that retains at least about 70%, 75%, 80%, 85%, 90%, 95% or 99% of its RI activity (as determined by activity assays described below in the Examples) upon exposure to or incubation at temperatures of at least about 45° C. to about 60° C., or at least about 51° C., 52° C., 53° C., 54° C., 55° C., 56° C., 57° C., 58° C., or 59° C., for about 1–5 minutes. Thus, the present invention also relates to a chimeric mammalian RI wherein the chimeric mammalian RI is thermostable. The chimeric RI comprises the portion or fragment of RI involved with thermostability. Such a thermostable portion, according to the invention, can be fused to RIs or to portions of RI which may have other beneficial features (e.g., specificity for a larger group or different types of RNases).

More particularly, the invention relates to nucleic acid molecules comprising a polynucleotide encoding a chimeric porcine/human RI. Such nucleic acid molecules may have any nucleotide sequence encoding a chimeric porcine/human RI according to the description above, including, for example, a nucleotide sequence at least about 90%, at least about 95% or at least about 99% identical to a reference sequence selected from the group consisting of (a) the nucleotide sequence set forth in SEQ ID NO:7, wherein T can also be U; and (b) a nucleic acid sequence complementary to (a). It will be apparent to the skilled artisan, however, that equivalent polynucleotides encoding a chimeric porcine/human RI, but having nucleotide sequences that may be different from that set forth in SEQ ID NO:7, may be prepared by the present methods and are therefore encompassed by the present invention. Since determined nucleotide sequences encoding a human liver RI polypeptide and two non-human mammalian RI polypeptides (specifically, porcine and rat liver RIs) are provided in SEQ ID NOs:5, 1 and 3, respectively, generating polynucleotides encoding a chimeric mammalian RI, such as a chimeric porcine/human RI or a chimeric rat/human RI, having nucleotide sequences different from that set forth in SEQ ID NO:7, could be accomplished using methods that are well-known in the art and that therefore would be routine to the skilled artisan.

Nucleic acid molecules of the present invention which encode a human liver RI polypeptide or a chimeric mammalian RI polypeptide may include, but are not limited to, those encoding the amino acid sequence of the mature polypeptides by themselves; the coding sequence for the mature polypeptides and additional coding sequences, such as those encoding a leader or secretory sequence, such as a pre-, or pro- or prepro- protein sequence; the coding sequence of the mature polypeptides, with or without the aforementioned additional coding sequences, together with additional, non-coding sequences, including for example introns and non-coding 5'and 3'sequences, such as the transcribed, untranslated regions (UTRs) or other 5'flanking sequences that may play a role in transcription (e.g., via providing ribosome- or transcription factor-binding sites), mRNA processing (e.g., splicing and polyadenylation signals) and stability of mRNA; the coding sequence for the mature human liver RI polypeptide (e.g., SEQ ID NO:5) or chimeric mammalian RI polypeptide (e.g., SEQ ID NO:7) operably linked to a regulatory DNA sequence, particularly a heterologous regulatory DNA sequence such as a promoter or enhancer; and the coding sequence for the mature human liver RI polypeptide or chimeric mammalian RI polypeptide linked to one or more coding sequences which code for amino acids that provide additional functionalities. Thus, the sequence encoding the polypeptide may be fused to a marker sequence, such as a sequence encoding a peptide which facilitates purification of the fused polypeptide. In certain embodiments of this aspect of the invention, the marker amino acid sequence may be a hexa-histidine peptide, such as the tag provided in a pQE vector (Qiagen, Inc.), among others, many of which are commercially available. As described for instance in Gentz et al., *Proc. Natl. Acad. Sci. USA* 86: 821–824 (1989), hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). Yet another useful marker peptide for facilitation of purification of human liver RI or a chimeric mammalian RI is glutathione S-transferase (GST) encoded by the pGEX fusion vector (see, e.g., Winnacker, *From Genes to Clones*, New York: VCH Publishers, pp. 451–481 (1987), or HSA (human Serum Albumin) binding domain encoded by pAff2c (Nilsson el al, *BioTechniques* 22: 744–751 (1997)). Other such fusion proteins include a human liver RI polypeptide (e.g., SEQ ID NO:5) or chimeric mammalian RI polypeptide (e.g., SEQ ID NO:7) fused to immunoglobulin Fc at the N- or C-terminus.

The present invention further relates to variants of the nucleic acid molecules of the present invention, which encode portions, analogs or derivatives of a human RI polypeptide or a chimeric mammalian RI polypeptide. Variants may occur naturally, such as a natural allelic variant. By an "allelic variant" is intended one of several alternate forms of a gene occupying a given locus on a chromosome of an organism (see Lewin, B., ed., *Genes II*, , John Wiley & Sons, New York (1985)). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of a human liver RI polypeptide or chimeric mammalian RI polypeptide or portions thereof Also especially preferred in this regard are conservative substitutions.

The present invention is directed to nucleic acid molecules at least about 90% or at least about 95% identical to the nucleic acid sequence set forth in SEQ ID NOs:5 and 7, or to the nucleic acid sequences of the deposited cDNAs, irrespective of whether they encode polypeptides having human liver RI activity or chimeric mammalian RI activity. This is because even where a particular nucleic acid molecule does not encode a polypeptide having human liver RI activity or chimeric mammalian RI activity, one of skill in the art would still know how to use the nucleic acid molecule, for instance, as a hybridization probe or a polymerase chain reaction (PCR) primer. Uses of the nucleic acid molecules of the present invention that do not encode a polypeptide having human liver RI or chimeric mammalian RI activity include, inter alia, (1) isolating the human liver RI gene or allelic variants thereof in a cDNA library; (2) in situ hybridization (e.g., "FISH") to metaphase chromosomal spreads to provide precise chromosomal location of the human liver RI gene, as described for human gene localization in Verma e al., *Human Chromosomes. A Manual of Basic Techniques*, Pergamon Press, New York (1988); and (3) northern blot analysis for detecting human liver RI mRNA expression in specific tissues or chimeric mammalian RI expression in, for example, the tissues of a transgenic animal.

Of course, due to the degeneracy of the genetic code, one of ordinary skill in the art will immediately recognize that a large number of the nucleic acid molecules having a sequence at least about 90% or at least about 95% identical to the nucleic acid sequences of the deposited cDNAs or the nucleic acid sequences set forth in SEQ ID NOs:5 and 7 will encode polypeptides having human liver RI or chimeric mammalian RI polypeptide structure and/or activity. In fact, since degenerate variants of these nucleotide sequences all encode the same polypeptide, this will be clear to the skilled artisan even without performing the above described comparison assay. It will be further recognized by one of ordinary skill in the art that, for such nucleic acid molecules that are not degenerate variants, a reasonable number will also encode polypeptides having human liver RI or chimeric mammalian RI polypeptide structure and/or activity. This is because the skilled artisan is fully aware of amino acid substitutions that are either less likely or unlikely to significantly affect protein function (e.g., replacing one aliphatic amino acid with a second aliphatic amino acid). For example, guidance concerning how to make phenotypically silent amino acid substitutions is provided in Bowie, J. U., et al., *Science* 247: 1306–1310 (1990), and the references cited therein.

The invention also relates to isolated nucleic acid molecules comprising polynucleotides which hybridize under stringent hybridization conditions, as defined above, to a portion of a polynucleotide having a nucleotide sequence identical to the nucleotide sequence of the above-described nucleic acid molecules. By a polynucleotide which hybridizes to a "portion" of a polynucleotide is intended a polynucleotide (either DNA or RNA) hybridizing to at least about 15 nucleotides, and more preferably at least about 20 nucleotides, still more preferably at least about 30 nucleotides, and even more preferably about 30–70 nucleotides of the reference polynucleotide. These hybridizing polynucleotides are useful, for example, as probes and primers as discussed above.

Of course, polynucleotides hybridizing to a larger portion of the reference polynucleotide (e.g., a nucleic acid molecule comprising a human liver RI or a chimeric mammalian RI gene having the nucleotide sequences set forth in SEQ ID NOs:5 and 7, respectively), for instance, a portion about 50–200 nucleotides in length, or even to the entire length of the reference polynucleotide, are also useful as probes according to the present invention, as are polynucleotides corresponding to most, if not all, of the nucleotide sequences set forth in SEQ ID NOs:5 and 7. By a portion of a polynucleotide of "at least 20 nucleotides in length," for example, is intended 20 or more contiguous nucleotides from the nucleotide sequence of the reference polynucleotide (e.g., the nucleotide sequences as set forth in SEQ ID NOs:5 and 7). As indicated, such portions are useful diagnostically either as a probe according to conventional DNA hybridization techniques or as primers for amplification of a target sequence by the polyinerase chain reaction (PCR), as described, for instance, in *Molecular Cloning A Laboratory Manual*, 2nd edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference.

Since determined nucleotide sequences encoding a human liver RI polypeptide and a chimeric porcine/human RI polypeptide are provided in SEQ ID NOs:5 and 7, respectively, generating polynucleotides which hybridize to a portion of the human liver RI cDNA molecule or a chimeric porcine/human RI cDNA molecule would be routine to the skilled artisan. For example, restriction endonuclease cleavage or shearing by sonication of the above-described cDNA clones could easily be used to generate DNA portions of various sizes which are polynucleotides that hybridize to a portion of the human liver RI cDNA molecule or the chimeric porcine/human cDNA molecule. Alternatively, the hybridizing polynucleotides of the present invention could be generated synthetically according to known techniques.

The invention also relates to such nucleic acid molecules which may further comprise one or more nucleotide sequences encoding one or more binding peptides, which sequences are preferably located 5'to the translation start site of the polynucleotides encoding the human liver RI or the chimeric mammalian RI. Binding peptides according to this aspect of the invention may include those described in detail above.

The invention also relates to these nucleic acid molecules, with or without the sequences encoding one or more binding peptides, wherein the nucleic acid molecules encoding the human liver RI or chimeric mammalian RI are operably linked to a promoter for expression of human liver RI or a chimeric mammalian RI. Examples of such promoters, and methods of operably linking the nucleic acid molecules of the invention to these promoters, are as described above.

The invention also relates to vectors comprising the above-described nucleic acid molecules, which may be expression vectors comprising the nucleic acid molecule operably linked to a promoter, which may be an inducible promoter under the control of a repressor such as lacI$^q$. The invention also relates to host cells comprising these nucleic acid molecules or vectors. Particularly preferred host cells include those described above, particularly *Escherichia coil* cells and most particularly *Escherichia coli* strains DH10B and DH5αF'IQ (available from LTI, Rockville, Md.).

The invention also relates to methods for producing a human liver RI polypeptide, and to methods for producing a chimeric mammalian RI polypeptide (particularly a chimeric porcine/human RI polypeptide) which may be thermostable. Methods according to this aspect of the invention may comprise culturing one or more of the above-described host cells under conditions suitable for the expression of the nucleic acid molecule encoding the human liver RI, or the chimeric mammalian RI, by the host cells, and isolating a human liver RI polypeptide or a chimeric mammalian RI polypeptide. Techniques for introducing nucleic acids into a host cell, culturing the host cell and isolating a polypeptide produced by the host cell are as generally described above, and more fully in the Examples below.

The invention also relates to a human liver RI polypeptide produced according to these methods. In particular, the invention provides an isolated human liver RI polypeptide having the amino acid sequence encoded by a polynucleotide having the nucleotide sequence set forth in SEQ ID NO:5 or by the deposited cDNA clone, the complete amino acid sequence set forth in SEQ ID NO:6, or a peptide or polypeptide comprising a portion of the above polypeptides. In addition, the invention relates to a chimeric mammalian RI polypeptide produced according to these methods, particularly a chimeric porcine/human (preferably human liver or placental) RI polypeptide which may be thermostable. In particular, the invention provides an isolated chimeric mammalian RI polypeptide having the amino acid sequence encoded by a polynucleotide having the nucleotide sequence set forth in SEQ ID NO:7, the complete amino acid sequence set forth in SEQ ID NO:8, or a peptide or polypeptide comprising a portion of the above polypeptides.

As used herein, the terms "peptide" and "oligopeptide" are considered synonymous (as is commonly recognized) and each term can be used interchangeably as the context requires to indicate a chain of at least two amino acids coupled by (a) peptide linkage(s). The term "polypeptide" is used herein to denote chains comprising ten or more amino acid residues. As is commonly recognized in the art, all oligopeptide and polypeptide formulas or sequences herein are written from left to right and in the direction from amino terminus to carboxy terminus.

It will be recognized by those of ordinary skill in the art that some amino acid sequences of the human liver RI polypeptide or chimeric mammalian polypeptide can be varied without significant effect on the structure or function of the polypeptide. If such differences in sequence are contemplated, it should be remembered that there will be critical areas on the protein which determine structure and activity. In general, it is possible to replace residues which form the tertiary structure, provided that residues performing a similar function are used. In other instances, the type of residue may be completely unimportant if the alteration occurs at a non-critical region of the polypeptide.

Thus, the invention further includes variants or mutants of the human liver RI polypeptide or chimeric mammalian RI polypeptide, including allelic variants, which show substantial structural homology to or activity of a human liver RI or chimeric mammalian RI polypeptide. Such variants or mutants may include deletions, insertions, inversions, repeats, and type substitutions (for example, substituting one hydrophilic strongly r another, but not strongly hydrophilic for strongly hydrophobic as a rule). Small changes or such "neutral" amino acid substitutions will generally have little effect on activity.

Typical conservative substitutions are the replacements, one for another, among the aliphatic amino acids Ala, Val, Leu and Ile, interchange of the hydroxylated residues Ser and Thr; exchange of the acidic residues Asp and Glu; substitution between the amidated residues Asn and Gln; exchange of the basic residues Lys and Arg, and replacements among the aromatic residues Phe and Tyr.

Thus, the fragment, derivative or analog of the polypeptides having amino acid sequences as set forth in SEQ ID NOs:6 or 8, or those encoded by polynucleotides having nucleic acid sequences as set forth in SEQ ID NOs:5 or 7 or by the deposited cDNA clone, may be (i) those in which one or more of the amino acid residues are substituted with a conserved or non-conserved amino acid residue (preferably a conserved amino acid residue), and such substituted amino acid residue may be encoded by the genetic code or may be an amino acid (e.g., desmosine, citrulline, ornithine, etc.) that is not encoded by the genetic code; (ii) those in which one or more of the amino acid residues includes a substituent group (e.g., a phosphate, hydroxyl, sulfate or other group) in addition to the normal "R" group of the amino acid; (iii) those in which the mature polypeptide is fused with another compound, such as a compound to increase the half-life of the polypeptide (for example, polyethylene glycol), or (iv) those in which additional amino acids are fused to the mature polypeptide, such as an immunoglobulin Fc region peptide, a leader or secretory sequence, a sequence which is employed for purification of the mature polypeptide (such as GST) or a proprotein sequence. Such fragments, derivatives and analogs are intended to be encompassed by the present invention, and are within the scope of those skilled in the art from the teachings herein and the state of the art at the time of invention.

The polypeptides of the present invention are preferably provided in an isolated form, and preferably are substantially purified. A recombinantly produced version of the human liver RI polypeptide or chimeric mammalian RI polypeptide can be substantially purified by the one-step method described in Smith and Johnson, *Gene* 67: 31–40 (1988).

The polypeptides of the present invention include those which are at least 90% identical, more preferably at least 95% identical, and most preferably at least 96%, 97%, 98% or 99% identical to the polypeptides encoded by polynucleotides having nucleic acid sequences as set forth in SEQ ID NOs:6 or 8 or by the deposited cDNA, or to the polypeptides having the complete amino acid sequences set forth in SEQ ID NOs:5 or 7. The present polypeptides also include portions of the above-described polypeptides with at least 30 amino acids and more preferably at least 50 amino acids.

By a polypeptide having an amino acid sequence at least, for example, 95% "identical" to a reference amino acid sequence of a RI polypeptide is intended that the amino acid sequence of the polypeptide is identical to the reference sequence except that the polypeptide sequence may include up to five amino acid alterations per each 100 amino acids of the reference amino acid of the RI polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino (N-) or carboxy (C-) terminal positions of the reference amino acid sequence or anywhere between those terminal positions, interspersed either individually among residues in the reference sequence or in one or more contiguous groups within the reference sequence.

The invention also relates to a general method of producing ribonuclease inhibitor which is substantially free of RNase activity. Such methods apply to purification of any ribonuclease inhibitor, regardless of the source. Thus, the general method of the invention relates to isolating substantially RNase free ribonuclease inhibitor from a biological sample (e.g., cells, tissue, skin, brain, liver, kidney, etc.) obtained from any mammalian source (e.g., human, rat, porcine, canine, ovine, feline, monkey, ape, bovine, equine, chimeric mammalian, etc.). In particular, the method of the invention for obtaining substantially RNase free ribonuclease inhibitor comprises (a) obtaining a biological sample from a mammalian source which contains a ribonuclease inhibitor, (b) mixing said sample with a binding partner, with the proviso that said binding partner is not an RNase, and (c) isolating ribonuclease inhibitor bound to said binding partner. In accordance with the invention, the binding partner may be any molecule, other than RNase, which reversibly binds ribonuclease inhibitor. Preferably, such binding partner is an antibody or an antibody fragment (e.g., Fab) having specificity for ribonuclease inhibitor, although other suitable binding partners will be readily apparent to one of skill in the art. In the preferred method of the invention, ribonuclease inhibitor is isolated or purified by affinity chromatography, wherein said binding partner is attached to a solid support (e.g., any column matrix including but not limited to sepharose, agarose, hydroyapatite, etc.).

The invention also provides a general method for obtaining recombinant ribonuclease inhibitor which is substantially free of RNase activity. Such a method is suitable for isolating and purifying any recombinant ribonuclease inhibitor, regardless of the type of the ribonuclease inhibitor (e.g., human, bovine, porcine, rat, bovine, canine, feline, equine, ovine, monkey, ape, chimeric mammalian, etc.) and regardless of the recombinant host used to express the ribonuclease inhibitor. In this method of the invention, substantially RNase free recombinant ribonuclease inhibitor is obtained by (a) culturing a recombinant host under conditions sufficient to express ribonuclease inhibitor, (b) mixing the ribonuclease inhibitor with a binding partner, with the proviso that the binding partner is not an RNase, and (c) isolating the ribonuclease inhibitor bound to the binding partner. In accordance with this aspect of the invention, the binding partner may be any molecule which binds to the ribonuclease inhibitor (e.g., antibodies and fragments thereof) provided however that said binding partner is not RNase.

Preferably, the recombinant ribonuclease is expressed in a modified form which allows selective binding to the binding partner. Such modifications which allow the isolation of a desired protein with a binding partner will be apparent to one skilled in the art. Preferably, the RI is modified to comprise a peptide to form a fusion protein which specifically binds to the binding partner (referred to herein as a "binding peptide"). Such peptide tags are well known in the art. Preferred peptide tags include His tag, thioredoxin tag, hemagglutinin tag, GST tag, HSA binding tag, and OmpA signal sequence tag. As will be understood, the binding partner which recognizes and binds to the binding peptide may be any molecule or compound including metal ions (e.g., metal affinity columns), antibodies or fragments thereof and any protein or peptide which binds the binding peptide. Thus, the invention relates to a method of obtaining substantially RNase free recombinant ribonuclease inhibitor comprising (a) culturing a recombinant host under conditions sufficient to express a ribonuclease inhibitor which comprises a binding peptide, (b) mixing the ribonuclease inhibitor with a binding partner which is capable of binding to the binding peptide, and (c) isolating the ribonuclease inhibitor bound to said binding partner. Preferably, the binding partner which binds the binding peptide is bound to a solid support (e.g., affinity chromatography).

The method of the invention may also comprise removing the binding peptide from RI after isolating or purifying the recombinant RI. Such removal may be accomplished by well known chemical and enzymatic techniques.

Uses

The RIs of the invention may be used for a variety of purposes, in industrial, clinical, forensic, research and other settings. The RIs of the present invention can be used as molecular weight markers on SDS-PAGE gels or on molecular sieve gel filtration columns using methods well known to those of skill in the art. In addition, the RIs of the invention may be used in synthesis of nucleic acid molecules, in vitro synthesis of polypeptides, and in situ transcription (IST) (Chang, H., *J. Immunol. Methods.* 176: 235–243 (1994)).

Production of Nucleic Acid Molecules

The RIs of the present invention may be used in methods for the production of nucleic acid molecules. Methods according to this aspect of the invention may comprise, for example, mixing a template nucleic acid molecule, which may be an RNA molecule such as a MRNA or polyA+RNA molecule, with one or more of the RI polypeptides of the invention (such as one or more human liver RI polypeptides or chimeric mammalian, particularly porcine/human, RI polypeptides) under conditions sufficient to synthesize a nucleic acid molecule from the template nucleic acid molecule. Preferably, thermostable RIs are used in this method. Appropriate conditions for production of nucleic acid molecules are known in the art (see, e.g., Sambrook, J., et al., *Molecular Cloning: A Laboratory Manual,* 2nd Ed., Cold Spring Harbor, N.Y.: Cold Spring Harbor Laboratory Press (1987)), and will be familiar to one of ordinary skill.

The mixtures may further comprise one or more polypeptides having reverse transcriptase activity, such as M-MLV reverse transcriptase, RSV reverse transcriptase, AMV reverse transcriptase, RAV reverse transcriptase, MAV reverse transcriptase or HIV reverse transcriptase. These polypeptides having reverse transcriptase activity may be substantially reduced in RNase H activity; preferred such polypeptides include M-MLV H⁻reverse transcriptase, RSV H⁻reverse transcriptase, AMV H⁻reverse transcriptase, RAV H⁻reverse transcriptase, MAV H⁻reverse transcriptase and HIV H⁻reverse transcriptase. Optimal concentrations, formulations, etc., for use of polypeptides having reverse transcriptase activity, which may be substantially reduced in RNase H activity, in production of nucleic acid molecules according to the methods of the present invention are disclosed, for example, in co-pending U.S. application Ser. No. 60/044,589, filed Apr. 22, 1997, the disclosure of which is incorporated by reference herein in its entirety.

By an enzyme "substantially reduced in RNase H activity" is meant that the enzyme has less than about 20%, more preferably less than about 15%, 10% or 5%, and most preferably less than about 2%, of the RNase H activity of a wildtype or RNase H' enzyme such as wildtype Moloney Murine Leukemia Virus (M-MLV) or Avian Myeloblastosis Virus (AMV) reverse transcriptases The RNase H activity of any enzyme may be determined by a variety of assays, such as those described, for example, in U.S. Pat. No. 5,244,797, in Kotewicz, M. L., et al., *Nucl. Acids Res.* 16: 265 (1988) and in Gerard, G. F., et al., *FOCUS*14(5): 91 (1992), the disclosures of all which are fully incorporated herein by reference.

According to this aspect of the invention, the mixture may further comprise one or more thermostable DNA polymerases such as Tne, Tma, Taq, Pfu, Tth, Tfi, VENT, DEEPVENT, Pwo or Tfl polymerases, or mutants, variants and derivatives thereof Optimal concentrations, formulations, etc., for use of thermostable DNA polymerases in production of nucleic acid molecules according to the methods of the present invention are disclosed, for example, in co-pending U.S. application Ser. Nos. 08/689,815, filed Aug. 14, 1996, 08/778,082, filed Jan. 2, 1997, and 08/801,720, filed Feb. 14, 1997, the disclosures of which are incorporated by reference herein in their entireties.

The mixtures used in the present methods may also optionally comprise one or more polypeptides having RNA polymerase activity.

According to the invention, the methods for producing a nucleic acid molecule may be conducted using automated thermocycling, particularly since the human liver RIs and chimeric mammalian RIs (such as the chimeric porcine/human RI) of the invention are thermostable. Thus, the methods of the invention may be performed at temperatures of from about 45° C. to about 70° C., from about 50° C. to about 65° C., from about 55° C. to about 60° C., from about 56° C. to about 60° C., from about 57° C. to about 60° C., from about 58° C. to about 60° C., from about 59° C. to about 60° C., or at temperatures of about 50° C. or greater, about 51° C. or greater, about 52° C. or greater, about 53° C. or greater, about 54° C. or greater, about 55° C. or greater, about 56° C. or greater, about 57° C. or greater, about 58° C. or greater, about 59° C. or greater, about 60° C. or greater, about 61° C. or greater, about 62° C. or greater, about 63° C. or greater, about 64° C. or greater or about 65° C. or greater.

The invention also relates to nucleic acid molecules produced according to these methods, which may be DNA molecules (including cDNA molecules or libraries), RNA molecules or DNA-RNA hybrid molecules. Nucleic acid molecules produced according to the methods of the invention may be full-length nucleic acid molecules (e.g, full-length cDNAs or RNAs) or fragments thereof, and may be single-stranded or double-stranded.

In a preferred aspect of the invention, the method of nucleic acid synthesis concerns the use of mRNA as a template to make cDNA or a cDNA library. Such method may comprise (a) contacting an mRNA template or population of nmRNA molecules (obtained from a cell or tissue of biological sample) with one or more RI's of the invention and (b) incubating said mixture under conditions sufficient to make one or more DNA molecules (e.g cDNA) complementary to all or a portion of said template or said population of molecules. The synthesized DNA molecules may then be used as templates for further nucleic acid synthesis to make, for example, double stranded DNA molecules (e.g. double stranded cDNA) from the single stranded templates. In a preferred aspect, the synthesis of DNA molecules is accomplished by well known amplification techniques such as polymerase chain reaction (PCR).

In Vitro Polypeptide Production

In an alternative use, the RIs of the present invention may be used in methods for the in vitro production of polypeptides. Methods according to this aspect of the invention may comprise, for example, mixing a mRNA or polyA+RNA molecule with one or more of the RIs of the invention (such as a porcine liver, rat liver, human liver or chimeric mammalian (particularly a chimeric porcine/human) RI polypeptide), under conditions sufficient to translate a polypeptide from the mRNA or polyA+RNA molecule. Such conditions may comprise mixing the RNA molecule and one or more RIs of the invention with one or more cell-free protein translation systems that are known in the art, such as rabbit reticulocyte lysate, wheat germ extract, etc. (see Walter, P., and Blobel, G., *J. Cell Biol.* 91: 557 (1981); Sambrook, J., et al., *Molecular Cloning: A Laboratory Manual,* 2nd Ed., Cold Spring Harbor, N.Y.: Cold Spring Harbor Laboratory Press, pp. 18.79–18.80 (1987); Kaufman, P. B., et al., *Handbook of Molecular and Cellular Methods in Biology and Medicine,* Boca Raton, Fla.: CRC Press, pp. 318–322 (1995)). Alternatively, the RIs of the invention may be used to produce polypeptides in automated or semi-automated protein synthesis methodologies that will be familiar to the skilled artisan.

The invention also relates to polypeptides produced according to these methods. Polypeptides produced by these methods may include full-length polypeptides or any fragment thereof In Vitro Transcription In an alternative use, the RIs of the present invention may be used in methods for the in vitro production of a nucleic acid molecule from a template nucleic acid molecule template (i.e., in vitro transcript this aspect of to this aspect of the invention may comprise, for example, mixing a nucleic acid molecule (which may be single-stranded or double-stranded and which is preferably a DNA molecule, a cDNA or an RNA molecule such as a mRNA molecule) with one or more of the RIs of the invention (such as a porcine liver, rat liver, human liver or chimeric mammalian (particularly a chimeric porcine/human) RI polypeptide), under conditions sufficient to produce a nucleic acid molecule from the template. Such conditions may comprise mixing the template nucleic acid molecule (preferably a DNA or cDNA molecule) and one or more RIs of the invention with one or more nucleotides (such as those described above) and one or more RNA polymerases that are known in the art (see Sambrook, J., et al., *Molecular Cloning: A Laboratory Manual,* 2nd Ed., Cold Spring Harbor, N.Y.: Cold Spring Harbor Laboratory Press (1987); Kaufman, P. B., et al., *Handbook of Molecular and Cellular Methods in Biology and Medicine,* Boca Raton, Fla.: CRC Press (1995)), to produce one or more MRNA molecules. Alternatively, these conditions may comprise mixing the template nucleic acid molecule (preferably an mRNA molecule) and one or more RIs of the invention with one or more nucleotides (such as those described above), one or more polypeptides having reverse transcriptase activity and/or one or more polypeptides having DNA polymerase activity, particularly those described above and most particularly those polypeptides having RT and/or DNA polymerase activity which are also thermostable, to produce one or more DNA molecules which may be single-stranded or double-stranded. In addition to isolated nucleic acid molecules, such methods may also be performed using whole cells or tissues or extracts thereof; if the nucleotides included in the reaction mix are also detectably labeled (e.g., with fluorescent or radioactive labels), these methods of the invention may be used to label specific nucleic acid sequences in fixed cells or tissues (see Chang, H, *J. Immunol. Meth.* 176(2): 235–243 (1994)).

Kits

The invention is also directed to kits comprising one or more containers containing one or more of the RIs of the invention. Kits according to this aspect of the invention may further comprise additional containers containing, for example, one or more of the thermostable DNA polymerases, polypeptides having reverse transcriptase activity or polypeptides having RNA polymerase activity described above. Additional kits of the invention may further comprise one or more containers containing a cell-free protein translation mixture, such as a rabbit reticulocyte lysate or a wheat germ extract. The kits of the invention may also optionally comprise one or more additional containers containing other reagents necessary for synthesis and analysis of nucleic acids or polypeptides, such as one or more buffers, one or more detergents, one or more deoxyribonucleoside triphosphates, one or more ribonucleoside triphosphates, agents for electrophoresis (e.g., acrylamide or agarose), and the like.

It will be readily apparent to one of ordinary skill in the relevant arts that other suitable modifications and adaptations to the methods and applications described herein are obvious and may be made without departing from the scope of the invention or any embodiment thereof Having now described the present invention in detail, the same will be more clearly understood by reference to the following examples, which are included herewith for purposes of illustration only and are not intended to be limiting of the invention.

EXAMPLES

Example 1

Cloning and Expression of Rat Liver RI in *E. coli*

To clone the gene encoding rat liver RI, total mRNA was isolated from rat liver, and first strand cDNA synthesis was accomplished using the protocol as previously described (Nathan, M. et al., *Focus* 17: 78–80 (1995)). The oligonucleotide used at the 5'-end of the gene was 5' TAA TAG CAT ATG AGT CTT GAC ATC CAG TGT GAG 3' (SEQ ID NO:9). The oligonucleotide used at the 3'-end of the gene was 5' TTA TTA GGA TCC TTA TCA GGA AAT GAT CCT CAG GGA TGG CC 3' (SEQ ID NO:10). An NdeI and a BamHI site were created in the oligonucleotide (bold and underlined) for easy cloning into an expression vector. The oligonucleotides were designed based on the cDNA sequence of rat lung RI cDNA, and were obtained from Life Technologies, Inc. (LTI; Rockville, Md.).

PCR was done using the PCR Supermix (LTI), which contains Taq DNA polymerase, plus about 10–20 ng of cDNA and oligonucleotides at a concentration of 2.5 $\mu$M. A Perkin-Elmer 9600 PCR machine was used to carry out the following cycling procedure: 1 cycle of 94° C. for 5 min.; 30 cycles of 94° C. for 20 sec./55° C. for 20 sec./72° C. for 1 min.; 1 cycle of 72° C. for 5 min.

The PCR fragment was digested with NdeI and BamHI and cloned into the pPROEX1 expression vector digested with NdeI and BamHI, which was obtained from LTI. This plasmid was then transformed into *E. coli* DH10B, a strain which was obtained from LTI. Six clones were picked to test whether they contained the cloned PCR product. Five out of the six clones contained the cloned fragment. One of the clones, pRatRI (FIG. 1), was grown to express the rat liver RI, the amino acid sequence of which is given in SEQ ID NO:4. Proteins isolated from induced cultures (40 ml) grown at 30° C. and 37° C. were analyzed by SDS-polyacrylamide gel electrophoresis (SDS-PAGE) (Laemmli, U. K., *Nature* 227: 680–685 (1970).

The pPROEX1 vector encodes 23 amino acid residues prior to the NdeI site. This region contains six histidine residues, a spacer region and a TEV-protease site. Thus, cloning at the NdeI site created a fusion protein containing an additional 23 amino acids at the amino terminus. Both the induced culture grown at 30° C. and the induced culture grown at 37° C. produced a protein slightly larger than 50 kD (about 52 kD), although RI purified from rat liver has a molecular weight of about 50 kD. The increase in the size of rat RI expressed from *E. coli* was due to the additional 24 amino acids corresponding to vector sequence. Although total RI protein production was higher at 37° C. than at 30° C., more soluble protein was produced at 30° C. Therefore, the cells appeared to produce more inclusion bodies at 37° C. than at 30° C.

Since the construction in pPROEX1 produced a fusion protein, an attempt to produce an unfused authentic rat liver RI was made. The NdeI-BamHI fragment from pRatRI was subcloned into pRE1 at the NdeI-BamHI sites. Plasmid pRE1, obtained from Dr. McKenney (Reddy, P. et al., *Nucleic Acids Res.* 17: 10473–10488 (1989)), is an expression vector containing a lambda pL promoter. The ligated material was introduced into CJ374 containing the repressor CI857 in a compatible chloramphenicol resistance plasmid (pCJ136). Six clones were tested for the presence of the cloned fragment, and six out of six clones contained the insert. One of the clones, pRERatRI (FIG. 2), was used to study the level of expression of RI.

Figure 2:
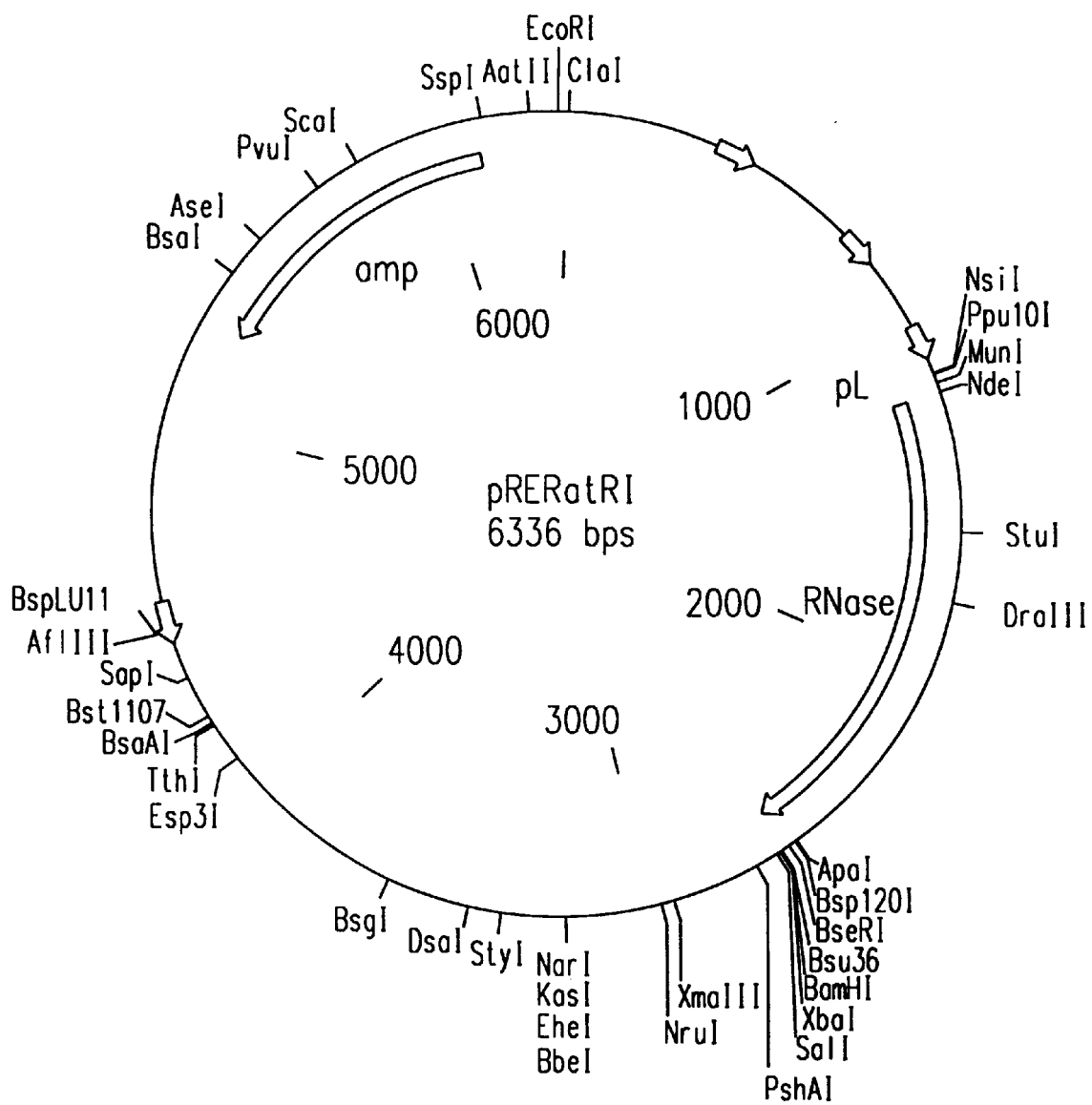
FIG. 2 is a map of plasmid pRERatRI.

A 50 ml culture was grown in rich medium (20 g NZ amine, 10 g Yeast Extract, 5 g NaCl, 2.5 g $K_2$ $HPO_4$, 0.4 g $MgSO_4$, 5 ml glycerol, pH 7.2), containing both ampicillin and chloramphenicol at 30° C. to an A590 of about 0.8. The culture was induced at 42° C. for 30 min and outgrown at 30° C. Samples were withdrawn for analysis by SDS-PAGE at different times. No induced protein around 50 kD was detected at any induction time point up to four hours. Surprisingly, rat RI was only produced as a fusion protein. In order to find out whether fusion is necessary for expression of rat liver RI, the RI coding sequence was fused with an OmpA signal sequence (21 amino acids) and cloned in pRE1 (FIG. 2). The cells were grown as described above, and the samples were analyzed by SDS-PAGE. An expressed protein of about 50 kD was detected in the induced sample but not in the uninduced samples. Since the expected size of fused protein was 52 kD, and the induced soluble protein was about 50 kD, it was apparent that the protein was made as a fused protein and later processed to authentic RI without the signal sequence. This confirms that rat RI protein expresses well when produced as a fusion protein in *E. coli*. However, the fusion partner is dispensable following expression, as was shown with the OmpA-RI fusion.

Example 2

Cloning and Expression of Porcine Liver RI

In order to obtain the gene encoding porcine liver RI, total mRNA was isolated from porcine liver, and first strand cDNA synthesis was accomplished using the protocol as previously described (Nathan, M. et al., Focus 17: 78–80 (1995)). Because the complete sequence of the porcine liver RI gene had not been established (Vincentini et al., Biochemistry 29: 8827–8834 (1990), the oligonucleotide used at the 5'-end of the gene corresponded to the amino-terminal amino acid sequence of porcine liver RI protein, while the oligonucleotide used at the 3'-end of the gene corresponded to the carboxy-terminal sequence of the porcine kidney RI gene. The nucleotide sequences of the oligonucleotide used at the 5'-end of the gene, which included an NdeI site (bold and underlined) was 5' TAT TAT <u>CAT ATG</u> AAC CTG/C GAC/T ATC/T CAC/T TGC/T GA 3' (SEQ ID NO:11). The oligonucleotide used at the 3'-end of the gene (bold and underlined) was 5' TAT TAT <u>AAG CTT</u> GCC CAA AAG GTG TTT TAC TAA GTA G 3' (SEQ ID NO:12).

PCR was carried out as described above in Example 1. The PCR products and the expression vector pPROEX1 were digested with NdeI and HindIII. The PCR products were then ligated into the vector, and the ligated material was introduced into DH10B, obtained from LTI. Surprisingly, very few clones were found. The PCR was repeated, and the fragment cloned again into pPROEX1. Only two out of 30 clones tested were found to have the insert. However, upon digestion with NdeI and HindIII, both clones generated a fragment of only about 1250 bp, rather than the 1500 bp of the PCR fragment. To confirm that the result was not a gel artifact, restriction digestion analysis was performed. The results suggest that the insert was indeed smaller than the PCR product. Interestingly, the two clones generated an identical restriction digestion profile.

The cloned fragment was also sequenced from both ends (see Example 3). The sequencing results indicated that both the amino and the carboxy termini of porcine liver RI were intact. These experiments indicate that the region deleted from the PCR fragment was internal to the porcine RI gene. The clone produced a protein of about 48 kD in size, smaller than the expected size of slightly greater than 50 kD. This smaller protein displayed no RI activity. From all of these experiments it was apparent that porcine RI is inhibitory to the growth of E. coli, and that the cloning procedure that was successful for obtaining the gene for rat liver RI was unsuitable for obtaining porcine liver RI. This result was surprising; as rat and porcine RI have 75% sequence identity, the clones were expected to have similar properties when expressed in E. coli. The reasons that porcine RI was difficult to clone and express in E. coli are unclear, but one theory is that porcine RI is so toxic to E. coli that the cell cannot express sufficient repressor in time to completely inhibit RI expression.

Figure 3:
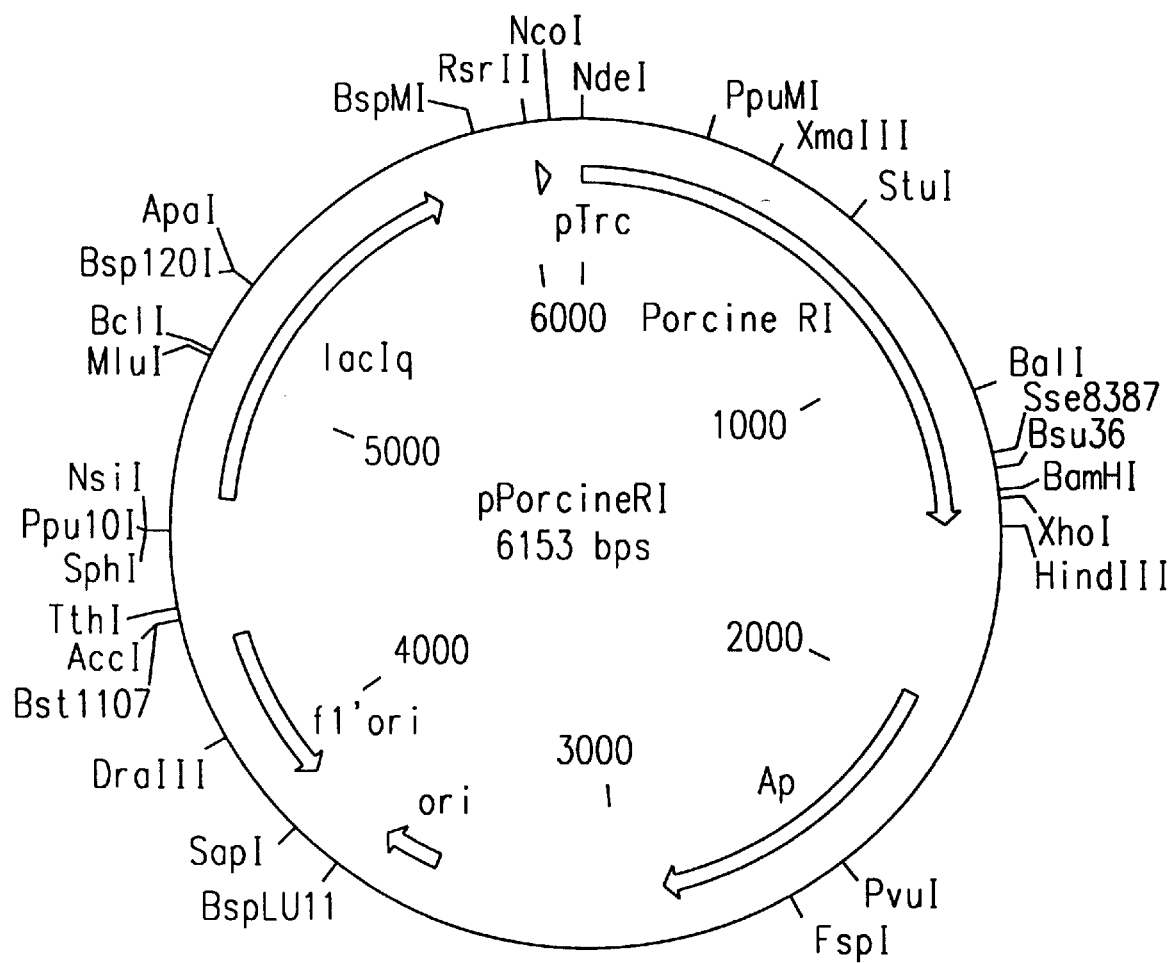
FIG. 3 is a map of plasmid pPorcineRI.

The 1500 bp PCR product of the porcine RI gene was then cloned into the vector pUC18 digested by NdeI and HindIII, which lacks a promoter to drive the gene. These clones were stable. The NdeI-HindIII fragment containing the porcine RI gene was then subcloned into pPROEX1 digested with NdeI and HindIII, and the resulting plasmid was introduced into DH5αF'IQ, a strain which constitutively expresses lacI$^q$ so that the repressor is present even before the introduction of the expression plasmid containing an additional copy of lacI$^q$. Twelve transformants were tested for the insert. 12 out of 12 clones generated a correct sized fragment. One of the clones, pPorcineRI (FIG. 3), was tested further for expression of porcine RI, the amino acid sequence of which is given in SEQ ID NO:2.

E. coli DH5αF'IQ containing pPorcineRI was grown to an A590 of between about 0.6–1.0 in a rich medium (20 g NZ amine, 10 g Yeast Extract, 5 g NaCl, 2.5 g K$_2$HPO$_4$, 0.4 g MgSO$_4$, 5 ml glycerol, pH 7.2) and 100 μg/ml ampicillin at 30° C. The culture was induced with IPTG (1.5 mM) for 3 hrs. The culture was spun down and the pellets were stored at −70° C. until used. The clone produced a protein slightly larger than 50 kD as expected. Thus, by the unusual procedure of preprotecting the expression of porcine RI, porcine liver RI was successfully cloned and expressed in E. coli. Upon induction, however, the growth rate of E. coli expressing porcine RI diminished considerably, whereas no inhibition of growth was observed in E. coli expressing rat liver RI.

The problems encountered in cloning and expressing porcine RI in E. coli allow a prediction that porcine RI will be active against E. coli RNases in addition to RNaseA, B and C.

Example 3

DNA Sequence Analysis of Porcine Liver RI

The nucleotide sequence of the 243 nucleotides (encoding 81 amino acids) at the 5'-end of the RI gene (SEQ ID NO:1, nucleotides 1–243; SEQ ID NO:2, amino acids 1–81) was obtained by methods known in the art. The amino acid sequence deduced from the nucleotide sequence of the cDNA matched perfectly with the amino acid sequence derived from direct sequencing of purified porcine RI.

Example 4

Purification of RI

All steps were carried out at 4° C. or on ice unless specified. The cells containing the recombinant plasmid were suspended at a 1:3 ratio (grains of cells ml buffer) in a buffer consisting of 50 mM Tris-HCl pH 8.0, 100 mM KCl, and 10 mM beta-mercaptoethanol (β-ME). The cell suspension was subjected to sonication using a sonicator (Heat Systems) until 80% of the cells were cracked as measured by A590. The cell debris was clarified by centrifugation. The supernatant was filtered through a 5 μm acrostic filter before loading onto a Ni-NTA-agarose affinity column equilibrated with 20 mM Tris-HCl, pH 8.0, 100 mM KCl, 10 mM β-ME, 10% glycerol. The column was washed with 10 column volumes of equilibration buffer containing 20 mM immidazole. The RI was eluted using a linear gradient of immidazole ranging from 20 mM to 150 mM in the same buffer. The fractions were analyzed by SDS-PAGE for the presence of a 52 kD protein, the apparent size of the fused RI.

Fractions containing the expected 52 kD protein were pooled and dialyzed in a buffer containing 20 mM Tris-HCl, pH 7.5, 10 mM dithiothrietol (DTT), 10% glycerol. The dialyzed material was loaded onto a MonoQ column (Pharmacia) equilibrated with the same buffer. The column was washed with 10 column volumes of the same buffer. The RI was eluted using a linear gradient of KCl ranging from 0 mM to 500 mM in the same buffer.

The fractions were analyzed by SDS-PAGE, and fractions containing a 52 kD protein were pooled. The pooled material was dialyzed in a storage buffer containing 20 mM Tris-HCl, pH 7.5, 50 mM KCl, 10 mM DTT, and 50% glycerol. The sample was tested for RNase inhibitor activity.

Example 5

Assay for RNase Inhibitor Activity

The activity of RI was determined essentially as described (Blackburn, P., et al., J. Biol Chem. 252: 5904–5910 (1977)).

RNase inhibitor activity was expressed by its ability to inhibit the activity of 5 ng of RNaseA (as measured by hydrolysis of yeast RNA) by 50%.

Example 6

Stabilization of RNase Inhibitor Activity

The addition of a chelator (e.g., EDTA) was found to stabilize storage of RNase inhibitor purified over a Ni-NTA agarose affinity column (see Example 4). Samples stored without chelator were found stable at 4° C. for less than one month, while RI stored in the month, while RI stored in the presence of a chelator were 1 st 6 months at 4° C. Thus, the invention relates generally to the use of a chelator to stabilize enzymes or proteins purified by a metal (e.g., Ni) column. The chelator effectively binds or removes the metal in the purified protein or enzyme, thus stabilizing the protein or enzyme.

Example 7

Cloning and Expression of Human Liver RI

Human liver cDNA was used as the template to amplify the RNase inhibitor gene. The oligonucleotides used were 5' TAT TAT CAT ATG AGC CTG GAC ATC CAG AGC CTG GA 3' (SEQ ID NO:13) (5' end) and 5' TAT TAG AAT TCA AGC TTA TCA GGA GAT GAC CCT CAG GGA 3' (SEQ ID NO:14) (3' end). An NdeI and a HindIII were created in the oligonucleotide for easy cloning, into an expression vector. PCR was done using LTI's PCR supermix, 25 ng of cDNA, and oligonucleotides at a concentration of 1.5 μM. A Perkin Elmer 9600 thermocycler was used to perform the PCRs using the following cycling protocol: 1 cycle at 94° C. for 5 minutes; 20 cycles of 94° C. for 20 seconds/55° C. for 20 seconds/72° C. for 1 minute; and 1 cycle at 72° C. for 5 minutes.

Figure 4:
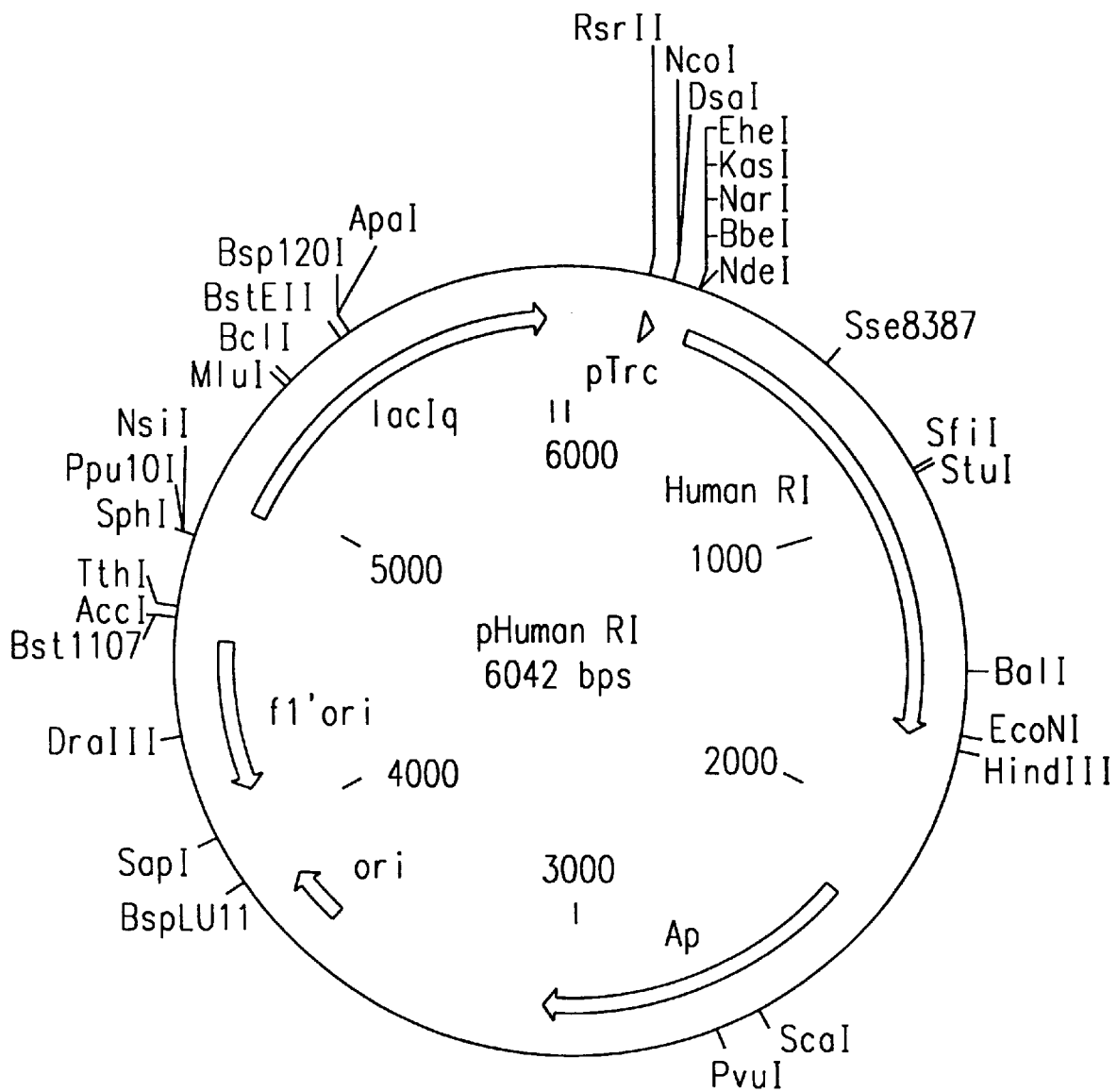
FIG. 4 is a map of plasmid pHumanRI.

The 1400 bp PCR product was digested with NdeI and HindIII and was cloned into the vectors pUC18 or pPROEX1. The PCR product was then ligated into the appropriately digested vector. The ligated material was introduced into competent DH5αF'IQ E. coli. Four of the eight clones in pUC18 had the desired insert whereas none of the eight in pPROEX was correct. The human liver RI was then subcloned into the expression vector pPROEX I as an NdeI/HindIII fragment, to produce pHumanRI (FIG. 4). All of the eight clones tested had the correct insert. When the clone was analyzed for protein expression by SDS-PAGE, a protein of about 52 kD was found to be produced. Upon sequencing, this protein was found to have the amino acid sequence set forth in SEQ ID NO:6.

The recombinant host cell comprising pHumanRI, E. coli DH5αF'IQ(pHumanRI), was deposited on Aug. 12, 1997, with the Collection, Agricultural Research Culture Collection (NRRL), 1815 North University Street, Peoria, Ill. 61604 USA, as Deposit No. NRRL B-21810.

Example 8

Cloning and Expression of Chimeric Porcine/ Human RI

Figure 5:
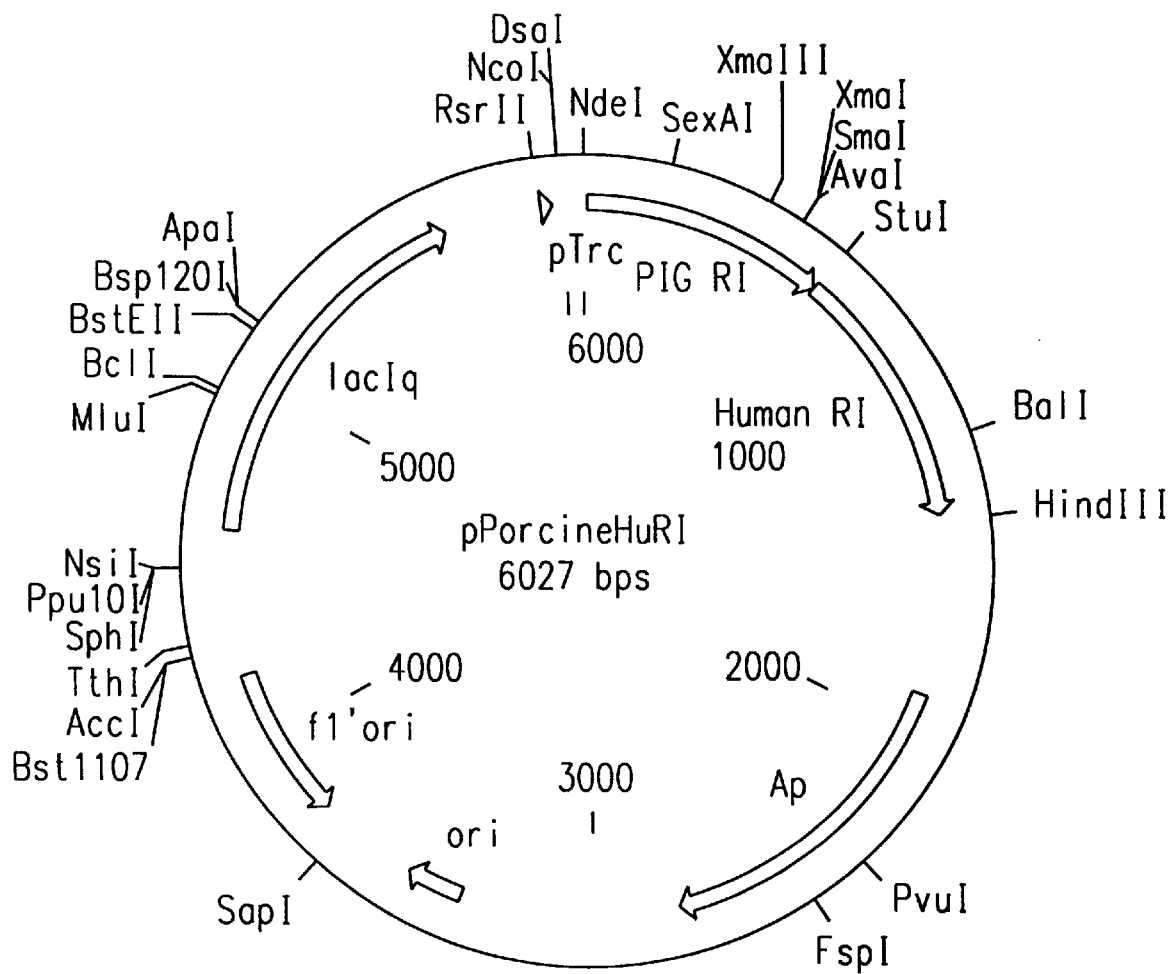
FIG. 5 is a map of plasmid pPorcineHuRI.

Sequence analysis of both the porcine RI and the human RI showed the presence of a single StuI site present ~700 bp away from the start of the RI gene. Oligonucleotides were designed to amplify the amino end and the carboxy end of the human liver RI. A StuI site was created in both the oligos. The oligonucleotides were 5' GTG GCC TCC AAG GCC TCG CTG CGG 3' (SEQ ID NO:15) to amplify the carboxy end and 5' CCG CAG CGA GGC CTT GGA GGC CAC 3' (SEQ ID NO:16) to amplify the amino end. The amino end of the porcine RI was amplified and the ~700 bp fragment was digested with the restriction enzymes NdeI and StuI. The human liver RI clone in the vector pPROEX I was digested with StuI and HindIII and the ~700 bp fragment was isolated. The plasmid pUC18 was digested with NdeI and HindIII and the three fragments were ligated. The ligated material was introduced into competent DH5αF'IQ E. coli. None of the eight clones tested had the right insert. Since the previous attempt involved ligating three fragments, which can prove problematic, a different strategy was used. The amino end of the porcine RI was amplified and the ~700 bp fragment was isolated after digesting it with NdeI and StuI. The human liver RI cloned into pUC18 was also digested with NdeI and StuI and the larger fragment which has the amino end deleted was isolated. The two fragments were ligated and introduced into competent DH5αF'IQ E. coli. Of the 12 clones tested, only one had the amino end of the porcine RI and the carboxy end of the human RI, as confirmed by restriction digestion analysis. This porcine/human chimeric RI was then subcloned into the expression vector pPROEX I as an NdeI/HindIII fragment. However, SDS-PAGE analysis of the expressed protein indicated that a ~32 kD protein was expressed, rather than the expected ~52 kD protein. The expression of this truncated protein may have been due to the StuI enzyme not cutting the PCR product; the ligation of the blunt fragment would then cause a frame shift resulting in a premature stop and thus expression of a truncated protein. Since this clone still had the StuI site, it was digested with NdeI and StuI and the ~700 bp fragment was ligated to the human liver RI cloned into pUC18 which was digested with NdeI and StuI to delete the amino end. Five of the nine clones tested were correct and the gene was then subcloned into the expression vector pPROEX I as an NdeI/HindIII fragment, to produce plasmid pPorcineHuRI (FIG. 5). SDS-PAGE analysis confirmed that a protein of ~52 kD was expressed by this construct. The clone was sequenced to confirm that the construct had the amino end of porcine RI and the carboxy end of human RI; the amino acid sequence of this chimeric polypeptide is set forth in SEQ ID NO:8.

Example 9

Purification and Characterization of Chimeric Porcine/Human RI

All steps were carried out at 4° C. or on ice unless stated. Host cells comprising plasmid pPorcineHuRI (see Example 8 and FIG. 5) were suspended in a buffer consisting of 50 mM Tris (pH 8.0), 100 mM KCl, and 10 mM β-mercaptoethanol (β-ME). The cell suspension was homogenized under pressure in a gaulin homogenizer until 85% of the cells were cracked as measured by A590. The cell debris was removed by centrifugation and the supernatant was loaded onto a chelating column (AF Chelate 650 M from TosoHaas) that was charged with nickel and equilibrated with 20 mM Tris pH 8.0, 100 mM KCl, 10 mM β-ME and 10% glycerol. The column was washed with 10 column volumes of equilibration buffer containing 20 mM imidazole. The RI was eluted with a linear gradient of imidazole from 20 mM to 150 mM in the same buffer. The fractions were analyzed by SDS-PAGE for the presence of the ~52 kD RI protein.

The fractions were pooled and dialyzed in a buffer containing 20 mM Tris (pH 8.0), 0.5 mM EDTA, 8 mM dithiothreitol (DTT) and 10% glycerol. The dialyzed material was loaded onto an anion exchange column (Source 30Q; Pharmacia) equilibrated in the same buffer. The column was washed with 10 column volumes of the same buffer and was eluted using a linear gradient of KCl from 0 mM to 500 mM in the same buffer.

The fractions were analyzed by SDS-PAGE and those containing the ~52 kD protein were pooled. This was dialyzed into a storage buffer containing 20 MM Tris (pH 8.0), 50 MM KCl, 0.5 mM EDTA, 8 mM DTT and 50% glycerol. Samples were tested for RNase inhibitor activity essentially by their ability to inhibit the hydrolysis of cyclic 2',3'-CMP by RNaseA (Blackburn, P., *J. Biol. Chem.* 254: 12484–12487 (1979)). One unit of inhibitor was that amount required to inhibit by 50% the activity of 5 ng of RNaseA.

Example 10

Thermostability of RIs

To determine the utility of the cloned RIs in high-temperature (i.e., above about 45° C.) reactions, 800 units of either cloned porcine RI or chimeric porcine/human RI were incubated on ice, or at 50° C., 55° C. or 60° C. for 5 minutes in a buffer containing 50 mM Bicine (pH 8.2), 115 mM potassium acetate, 8% glycerol and 2.5 mM manganese diacetate. The residual activity was determined by adding 2 μg RNase A and measuring the inhibition of hydrolysis of 0.2 mM cCMP by RNaseA.

The cloned porcine RI was found to be inactivated by incubation for five minutes at 55° C., while the chimeric porcine/human RI retained nearly 100% of its activity under these conditions. However, the chimeric porcine/human RI was inactivated by incubation for five minutes at 60° C. Similar thermostability assays indicated that rRNasin (recombinant human placental RI; Promega) retained its activity also retained its activity after incubation for five minutes at 55° C., while it was inactivated at 60° C. These results indicate that the cloned porcine/human chimeric RI of the invention is more thermostable than is fill-length porcine RI. Moreover, the thermostability of the porcine/human chimeric RI of the invention appears to be similar to that of a cloned human placental RI. These findings suggest that chimeric RIs comprising at least a portion of the human RI sequence may be useful in higher-temperature reactions, such as PCRs or RT-PCRs using automated thermocycling, which would be precluded by the use of thermolabile mammalian enzymes such as porcine RI.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. An isolated nucleic acid molecule comprising a polynucleotide encoding a chimeric ribonuclease inhibitor (RI), wherein said polynucleotide comprises a RI nucleotide sequence from a first mammalian species and a RI nucleotide sequence from a second mammalian species which is different from said first mammalian species, wherein said first and said second mammalian species are selected from the group consisting of rat, porcine, and human.

2. The nucleic acid molecule of claim 1, wherein said chimeric mammalian RI is thermostable.

3. The nucleic acid molecule of claim 1, wherein said first mammalian species is non-human and said second mammalian species is human.

4. The nucleic acid molecule of claim 3, wherein said human RI is a human liver RI or a human placental RI.

5. The nucleic acid molecule of claim 1, wherein said polynucleotide encodes a chimeric porcine/human RI.

6. The nucleic acid molecule of claim 5, wherein said polynucleotide has a nucleotide sequence selected from the group consisting of:
    (a) the nucleotide sequence set forth in SEQ ID NO:7, wherein T can also be U; and
    (b) a nucleic acid sequence complementary to (a).

7. The nucleic acid molecule of claim 6, wherein said polynucleotide has the nucleotide sequence set forth in SEQ ID NO:7.

8. An isolated nucleic acid molecule comprising a polynucleotide which hybridizes under stringent hybridization conditions to a polynucleotide having a nucleotide sequence identical to the nucleotide sequence of the nucleic acid molecule of claim 6.

9. The nucleic acid molecule of claim 1, further comprising one or more nucleotide sequences encoding one or more binding peptides.

10. The nucleic acid molecule of claim 9, wherein said nucleotide sequence encoding said binding peptide is located 5' to the translation start site of said polynucleotide encoding said chimeric mammalian RI.

11. The nucleic acid molecule of claim 9, wherein said binding peptide is selected from the group consisting of the OmpA signal sequence, a GST tag, a HIS tag, a thioredoxin tag and a hemaglutinin (HA) tag.

12. The nucleic acid molecule of claim 1, wherein said nucleic acid molecule is operably linked to a promoter for expression of said chimeric mammalian RI.

13. A vector comprising the nucleic acid molecule of claim 1.

14. The vector of claim 13, wherein said vector is an expression vector comprising said nucleic acid molecule operably linked to a promoter.

15. The vector of claim 14, wherein said promoter is an inducible promoter.

16. The vector of claim 15, wherein said inducible promoter is under the control of a repressor.

17. The vector of claim 16, wherein said repressor is lacI$^q$.

18. A host cell comprising the vector of claim 13.

19. A host cell comprising the nucleic acid molecule of claim 1.

20. A method for producing a chimeric mammalian RI polypeptide, said method comprising culturing the host cell of claim 19 and isolating said chimeric mammalian RI polypeptide.

21. The chimeric mammalian RI polypeptide of claim 20, wherein said polypeptide is thermostable.

22. A chimeric mammalian RI polypeptide produced by the method of claim 20.

23. The chimeric mammalian RI polypeptide of claim 22, wherein said polypeptide is a chimeric porcine/human RI polypeptide.

24. The isolated nucleic acid molecule of claim 1, wherein said RI from said first or second mammalian species is a rat liver RI.

25. The isolated nucleic acid molecule of claim 1, wherein said RI from said first or second mammalian species is a rat lung RI.

26. The isolated nucleic acid molecule of claim 1, wherein said RI from said first or second mammalian species is a porcine liver RI.

27. The isolated nucleic acid molecule of claim 1, wherein said RI from said first or second mammalian species is a human liver RI.

28. The isolated nucleic acid molecule of claim 1, wherein said RI from said first or second mammalian species is a human placental RI.

29. The isolated nucleic acid molecule of claim 1, wherein said chimeric RI has an amino acid sequence encoded by a polynucleotide having a nucleotide sequence as set forth in SEQ ID NO:7.

30. The isolated nucleic acid molecule of claim 1, wherein said chimeric RI has an amino acid sequence as set forth in SEQ ID NO:8.

31. The vector of claim 13, wherein said vector is plasmid pPorcineHuRI.

32. A kit comprising one or more containers, wherein a first container contains a chimeric mammalian RI.

33. The kit of claim 32, wherein said chimeric mammalian RI is a chimeric porcine/human liver RI.

34. The kit of claim 32, wherein said RI is thermostable.

35. The kit of claim 32, further comprising a container containing one or more thermostable DNA polymerases.

36. The kit of claim 35, wherein said thermostable DNA polymerases are selected from the group consisting of Tne, Tma, Taq, Pfu, Tth, Tfi, VENT, DEEPVENT, Pwo and Tfl.

37. The kit of claim 32, further comprising a container containing one or more polypeptides having reverse transcriptase activity.

38. The kit of claim 37, wherein said polypeptides having reverse transcriptase activity are substantially reduced in RNase H activity.

39. The kit of claim 37, wherein said polypeptides having reverse transcriptase activity are selected from the group consisting of M-MLV reverse transcriptase, RSV reverse transcriptase, AMV reverse transcriptase, RAV reverse transcriptase, MAV reverse transcriptase and HIV reverse transcriptase.

40. The kit of claim 38, wherein said polypeptides having reverse transcriptase activity that are substantially reduced in RNase H activity are selected from the group consisting of M-MLV H$^-$ reverse transcriptase, RSV H$^-$ reverse transcriptase, AMV H$^-$ reverse transcriptase, RAV H reverse transcriptase, MAV H$^-$ reverse transcriptase and HIV H$^-$ reverse transcriptase.

41. The kit of claim 32, further comprising a container containing one or more polypeptides having RNA polymerase activity.

42. The kit of claim 32, further comprising a container containing one or more cell-free protein translation mixtures.

43. The kit of claim 33, wherein said chimeric porcine/human RI has an amino acid sequence encoded by a polynucleotide having a nucleotide sequence as set forth in SEQ ID NO:7.

44. The kit of claim 33, wherein said chimeric porcine/human RI has an amino acid sequence as set forth in SEQ ID NO:8.

* * * * *

UNITED STATES PATENT AND TRADEMARK OFFICE
CERTIFICATE OF CORRECTION

PATENT NO. : 5,932,440
DATED : August 3, 1999
INVENTOR(S) : Chatterjee et al.

It is certified that error appears in the above-identified patent and that said Letters Patent is hereby corrected as shown below:

In column 53, line 58 (claim 21, line 1), please delete "20" and insert therein --22--.

In column 54, line 50 (claim 40, line 5), please delete "RAV H reverse" and insert therein --RAV H⁻ reverse--.

Signed and Sealed this

Twenty-ninth Day of February, 2000

Attest:

Q. TODD DICKINSON

Attesting Officer

Commissioner of Patents and Trademarks